US012576095B2

(12) United States Patent (10) Patent No.: US 12,576,095 B2
Warren et al. (45) Date of Patent: Mar. 17, 2026

(54) SYSTEMS AND METHODS FOR ACCURATE AND REPEATABLE DELIVERY OF ACTIVE PHARMACEUTICAL INGREDIENTS

(71) Applicant: Transport Authority, Inc., Dover, DE (US)

(72) Inventors: William Warren, Lafayette, CA (US); Walter Lee Smith, Danville, CA (US)

(73) Assignee: Transport Authority, Inc., Dover, DE (US)

( * ) Notice: Subject to any disclaimer, the term of this patent is extended or adjusted under 35 U.S.C. 154(b) by 483 days.

(21) Appl. No.: 17/944,920

(22) Filed: Sep. 14, 2022

(65) Prior Publication Data

US 2023/0077762 A1 Mar. 16, 2023

Related U.S. Application Data

(60) Provisional application No. 63/244,031, filed on Sep. 14, 2021.

(51) Int. Cl.
| | |
|---|---|
| *A61K 31/67* | (2006.01) |
| *A61J 3/00* | (2006.01) |
| *A61K 31/00* | (2006.01) |
| *A61K 31/4045* | (2006.01) |
| *A61K 31/675* | (2006.01) |

(52) U.S. Cl.
CPC ............... *A61K 31/675* (2013.01); *A61J 3/00* (2013.01); *A61K 31/4045* (2013.01); *A61K 31/658* (2023.05)

(58) Field of Classification Search
CPC .... A61K 31/675; A61K 31/05; A61K 31/352; A61K 31/4045; A61K 31/015; A61K 31/658; A61K 36/185; A61J 3/00; A61J 3/07; A61J 3/10; A61J 2200/70
See application file for complete search history.

(56) References Cited

U.S. PATENT DOCUMENTS

| | | | |
|---|---|---|---|
| 4,322,449 | A | 3/1982 | Voss et al. |
| 7,090,858 | B2 | 8/2006 | Jayaraman |
| 7,325,548 | B2 | 2/2008 | Enslin |
| 7,900,850 | B2 | 3/2011 | Zengerle et al. |
| 8,071,049 | B2 | 12/2011 | Koltay et al. |
| 8,910,630 | B2 | 12/2014 | Todd |
| 9,380,813 | B2 | 7/2016 | Mccullough |
| 9,474,304 | B2 | 10/2016 | Born et al. |

(Continued)

FOREIGN PATENT DOCUMENTS

| | | | |
|---|---|---|---|
| CA | 2984915 | A1 | 6/2017 |
| CA | 2969158 | A1 | 12/2018 |

(Continued)

OTHER PUBLICATIONS

Thompson et al., Sequential deposition of overlapping droplets to form a liquid line, J. Fluid Mech., 2014, vol. 761, 261-281.

(Continued)

*Primary Examiner* — Francis C Gray

(74) *Attorney, Agent, or Firm* — BakerHostetler

(57) ABSTRACT

This present disclosure provides reliable methods and apparatus for delivering microdroplets containing an active pharmaceutical ingredient (API) to underlying substrates. A control system is provided to ensure that the API dosage is both accurate and repeatable.

22 Claims, 8 Drawing Sheets

(56) References Cited

U.S. PATENT DOCUMENTS

| | | | |
|---|---|---|---|
| 9,526,792 | B1 | 12/2016 | Degeeter |
| 9,854,828 | B2 | 1/2018 | Langeland |
| 9,937,147 | B2 | 4/2018 | Degeeter |
| 9,974,333 | B1 | 5/2018 | Disner |
| 10,239,069 | B2 | 3/2019 | Rogers |
| 10,265,362 | B2 | 4/2019 | Schaneville |
| 10,369,178 | B2 | 8/2019 | Greenbaum et al. |
| 10,383,358 | B2 | 8/2019 | Kaplan et al. |
| 10,485,373 | B1 | 11/2019 | Millikin et al. |
| 2004/0086603 | A1* | 5/2004 | Shastry ................. C09D 11/30 426/104 |
| 2006/0000470 | A1* | 1/2006 | Clarke .............. G01N 21/9508 128/200.23 |
| 2006/0002986 | A1* | 1/2006 | Clarke ................ A61K 9/2072 424/443 |
| 2006/0003989 | A1* | 1/2006 | Quay .................... A61K 45/06 514/214.03 |
| 2007/0141198 | A1 | 6/2007 | Yang |
| 2007/0275333 | A1 | 11/2007 | Neuefeind et al. |
| 2008/0160787 | A1 | 7/2008 | Lehmann |
| 2009/0181080 | A1 | 7/2009 | Kottayil et al. |
| 2010/0136123 | A1 | 6/2010 | Izumida et al. |
| 2011/0177141 | A1 | 7/2011 | Celeste |
| 2012/0282317 | A1 | 11/2012 | Ekstein |
| 2013/0011523 | A1 | 1/2013 | Belzowski et al. |
| 2013/0011525 | A1 | 1/2013 | Belzowski et al. |
| 2013/0011529 | A1 | 1/2013 | Belzowski et al. |
| 2013/0087144 | A1 | 4/2013 | Todd |
| 2013/0089600 | A1 | 4/2013 | Winnicki |
| 2013/0184354 | A1 | 7/2013 | Jackson et al. |
| 2015/0257407 | A1 | 9/2015 | Glazier et al. |
| 2016/0051480 | A1 | 2/2016 | Taha |
| 2016/0256411 | A1 | 9/2016 | Aung-Din |
| 2016/0296474 | A1 | 10/2016 | Romanoschi et al. |
| 2016/0354561 | A1 | 12/2016 | Mccullough |
| 2017/0016836 | A1 | 1/2017 | Van Den Brink et al. |
| 2017/0050010 | A1 | 2/2017 | Mcallister et al. |
| 2017/0112188 | A1 | 4/2017 | Ostrander |
| 2017/0119660 | A1 | 5/2017 | Temtsin-Krayz et al. |
| 2017/0172977 | A1 | 6/2017 | Kleidon et al. |
| 2017/0196923 | A1 | 7/2017 | Moore |
| 2017/0245550 | A1 | 8/2017 | Freelander |
| 2017/0368021 | A1 | 12/2017 | Atkinson et al. |
| 2018/0117161 | A1 | 5/2018 | Docherty et al. |
| 2018/0140965 | A1 | 5/2018 | Flora et al. |
| 2018/0141277 | A1 | 5/2018 | Warner et al. |
| 2018/0221332 | A1 | 8/2018 | Renwick et al. |
| 2018/0297726 | A1 | 10/2018 | Ruben |
| 2019/0001087 | A1 | 1/2019 | Davidson et al. |
| 2019/0015383 | A1 | 1/2019 | Woelfel et al. |
| 2019/0022055 | A1 | 1/2019 | Siegel et al. |
| 2019/0030101 | A1 | 1/2019 | Cooper et al. |
| 2019/0073127 | A1 | 3/2019 | Ravindranath |
| 2019/0082728 | A1 | 3/2019 | Eaton |
| 2019/0116808 | A1 | 4/2019 | Tedeschi et al. |
| 2019/0192428 | A1 | 6/2019 | Goskonda et al. |
| 2019/0195852 | A1 | 6/2019 | Bryant et al. |
| 2019/0373679 | A1 | 12/2019 | Fu et al. |
| 2020/0330424 | A1 | 10/2020 | Bruun et al. |
| 2020/0352826 | A1* | 11/2020 | Warren .................. A23L 19/05 |
| 2020/0393480 | A1 | 12/2020 | Daume et al. |

FOREIGN PATENT DOCUMENTS

| | | |
|---|---|---|
| CA | 3040547 C | 12/2021 |
| CN | 109999932 A | 7/2019 |
| JP | 11-235164 A | 8/1999 |
| JP | 2006-504671 A | 8/2002 |
| JP | 2005-531330 A | 10/2005 |
| JP | 2013-521811 A | 6/2013 |
| JP | 2013-521812 A | 6/2013 |
| JP | 2013-521813 A | 6/2013 |
| JP | 2017-517295 A | 6/2017 |
| JP | 2018-505912 A | 3/2018 |
| JP | 2018-507262 A | 3/2018 |
| KR | 10-2011-0088991 A | 8/2011 |
| WO | 99/42000 A1 | 8/1999 |
| WO | 2004/016246 A1 | 2/2004 |
| WO | 2005/123569 A2 | 12/2005 |
| WO | 2015/164840 A1 | 10/2015 |
| WO | 2016/094810 A2 | 6/2016 |
| WO | 2016/141056 A1 | 9/2016 |
| WO | 2017/027528 A1 | 2/2017 |
| WO | 2019/014631 A1 | 1/2019 |
| WO | 2019/073127 A2 | 4/2019 |

OTHER PUBLICATIONS

Fan et al., "Development of a drop-on-demand droplet generator for one-drop-fill technology", Sensors and Actuators A: Physical, 147, 2008, 649-655.

Greenberg, Cannabis Scientists Are Chasing the Perfect High, The New York Times Magazine, https://www,nytimes.com/2020/04/01/magazine/cannabis-science.html, Apr. 1, 2020.

Hadzhykanova, E. "Edible Dosage Chart: How Much Is Enough", pp. 15, Honest Mariuana.pdf at Adobe Acrobat Pro (32 bit). (Year: 2016).

Helena Miles, "Microdosing Cannabis: The Ultimate Beginne s Guide", Wayback Machine—https://web.archive.Jrg/web/20191117102654/https://greencamp.com/microdosing, Feb. 14, 2019, pp. 1-6.

International Search Report and Written Opinion dated Jul. 29, 2020 issued in PCT/US2020/031128; 18 Pages.

JP-2006504671-A Machine Translation 31 pages (Year: 2006).

Levet et al., Formulation Development—Solubility-Enhancing Technologies in Pharmaceutical Development, a Mini-Review, Drug Development & Delivery, https://drug-dev.com/formulation-development-solubility-enhancing-technologies-in-pharmaceutical-development-a-mini-review/, Sep. 2024.

Miles, Helena, "Microdosing Cannabis: The Ultimate Beginner's Guide". The Ultimate Beginner_s.pdf. (Year: 2019).

Peshkovsky, Are Cannabinoids More Effective in Nano Form?, Sonomechanics Blog, Industrial Sonomechanics, May 28, 2016.

* cited by examiner

SYSTEMS AND METHODS FOR ACCURATE AND REPEATABLE DELIVERY OF ACTIVE PHARMACEUTICAL INGREDIENTS

CROSS-REFERENCE TO RELATED APPLICATIONS

This claims priority to U.S. Patent Application Ser. No. 63/244,031 filed Sep. 14, 2021, the disclosure of which is hereby incorporated by reference as if set forth in its entirety herein.

BACKGROUND

Field of the Art

The disclosure relates to the field of active pharmaceutical ingredients including cannabis, and methods and systems for ensuring accurate and repeatable dosing of same.

Discussion of the State of the Art

The legal cannabis industry is growing rapidly in the United States, Canada, and across the world. Cannabis, or other active pharmaceutical ingredient (API), are typically included in batch-produced food product or added after the food product has been fully prepared. Food products are sold having various dosages of the API indicated on the package labeling. Thus, it is a known objective to achieve dosage accuracy whereby the food product contains the dosages that are represented. It is another known objective to achieve dosage repeatability whereby different pieces of the same food product contain a substantially identical dosage. The dosage accuracy and repeatability provide the user with a predictable user experience when the food product is consumed or otherwise used.

Although claims are often made in the market that both objectives are achieved using conventional dosage techniques, wide variations both in dosage accuracy and dosage repeatability are common. As a result, the pharmaceutical effect that is experienced when consuming one piece of an individualized food product will substantially vary with respect to the pharmaceutical effect that is experienced when consuming another piece of the same individualized food product. The difference can have a profound impact when the food product is bite-sized. When the food product is larger than bite-sized, the variations of API dosing can further cause a first region of the food product to include substantially more or less API than a second region of the food product. Thus, the pharmaceutical effect that is experienced when consuming the first region of the food product will substantially vary with respect to the pharmaceutical effect that is experienced when consuming the second region of the food product.

What is therefore needed is a method and apparatus to reliably achieve dosage precision and consistency.

SUMMARY

In one example, a method of limiting error rates in a cannabinoid dosing system. The method can include the step of delivering microdroplets of a liquid successively from at least one dosing head to a substrate along a path, wherein the liquid contains a quantity of cannabinoid. The method can further include the step of imaging the successively delivered microdroplets at a location between the at least one dosing head and the substrate along the path. Based on the imaging step, the method can include the step of determining a total volume of the liquid that has been delivered to the substrate.

BRIEF DESCRIPTION OF THE DRAWINGS

The following detailed description will be better understood when read in conjunction with the appended drawings, in which there is shown in the drawings example embodiments for the purposes of illustration. It should be understood, however, that the present disclosure is not limited to the precise arrangements and instrumentalities shown. In the drawings.

DETAILED DESCRIPTION

Figures 1A, 1B:
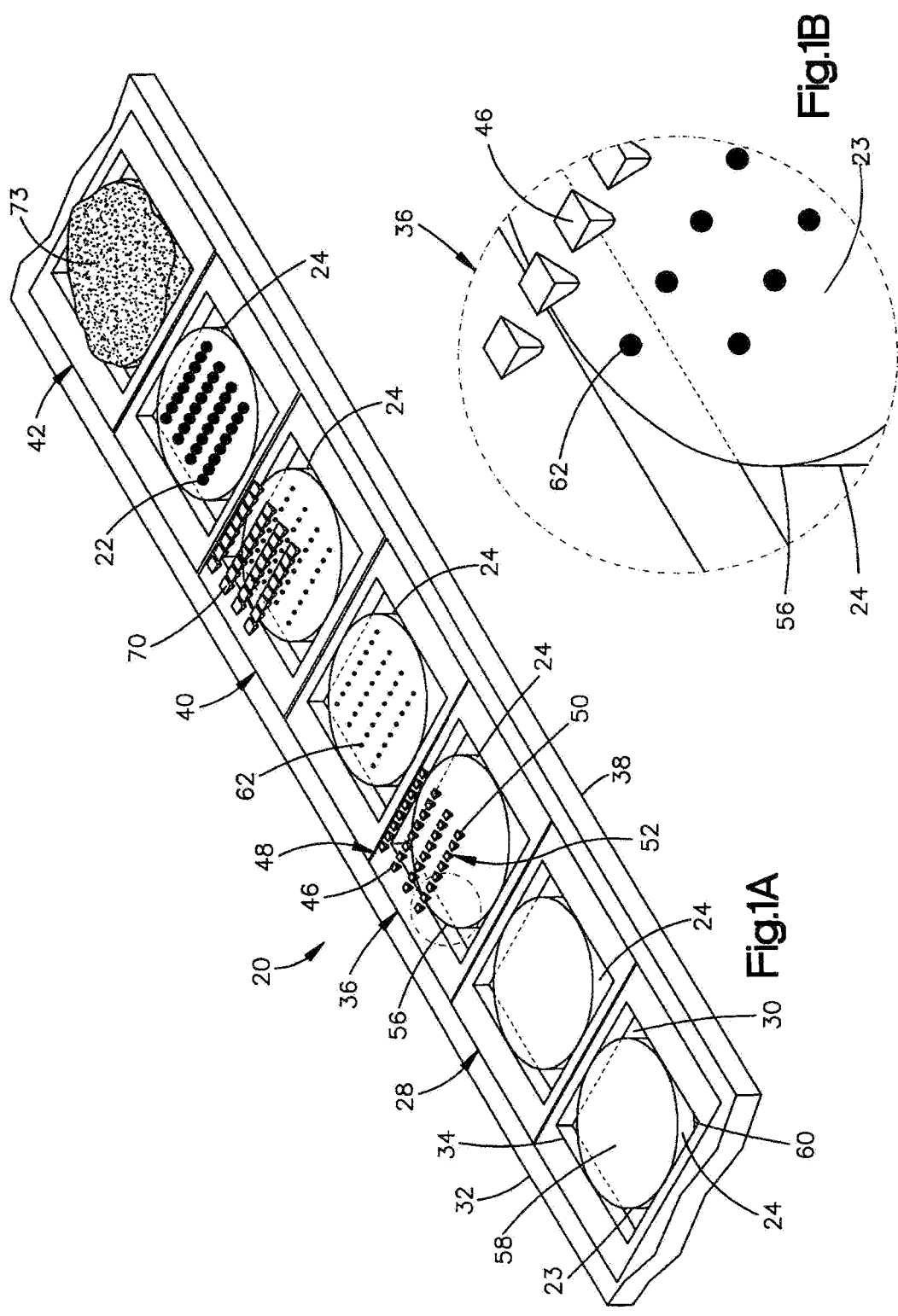
FIG. 1A is a schematic perspective view of an apparatus for delivering microdroplets of an active pharmaceutical ingredient to a substrate such as an edible product.
FIG. 1B is an enlarged schematic perspective view of a portion of the edible product illustrated in FIG. 1A.

One or more different aspects may be described in the present application. Further, for one or more of the aspects described herein, numerous alternative arrangements may be described; it should be appreciated that these are presented for illustrative purposes only and are not limiting of the aspects contained herein or the claims presented herein in any way. One or more of the arrangements may be widely applicable to numerous aspects, as may be readily apparent from the disclosure. In general, arrangements are described in sufficient detail to enable those skilled in the art to practice one or more of the aspects, and it should be appreciated that other arrangements may be utilized and that structural, logical, software, electrical and other changes may be made without departing from the scope of the particular aspects. Particular features of one or more of the aspects described herein may be described with reference to one or more particular aspects or figures that form a part of the present disclosure, and in which are shown, by way of illustration, specific arrangements of one or more of the aspects. It should be appreciated, however, that such features are not limited to usage in the one or more particular aspects or figures with reference to which they are described. The present disclosure is neither a literal description of all arrangements of one or more of the aspects nor a listing of features of one or more of the aspects that must be present in all arrangements.

Headings of sections provided in this patent application and the title of this patent application are for convenience only and are not to be taken as limiting the disclosure in any way.

Devices that are in communication with each other need not be in continuous communication with each other, unless expressly specified otherwise. In addition, devices that are in communication with each other may communicate directly or indirectly through one or more communication means or intermediaries, logical or physical.

A description of an aspect with several components in communication with each other does not imply that all such components are required. To the contrary, a variety of optional components may be described to illustrate a wide variety of possible aspects and in order to more fully illustrate one or more aspects. Similarly, although process steps, method steps, algorithms or the like may be described in a sequential order, such processes, methods and algorithms may generally be configured to work in alternate orders, unless specifically stated to the contrary. In other words, any sequence or order of steps that may be described in this patent application does not, in and of itself, indicate a requirement that the steps be performed in that order. The steps of described processes may be performed in any order practical. Further, some steps may be performed simultaneously despite being described or implied as occurring non-simultaneously (e.g., because one step is described after the other step). Moreover, the illustration of a process by its depiction in a drawing does not imply that the illustrated process is exclusive of other variations and modifications thereto, does not imply that the illustrated process or any of its steps are necessary to one or more of the aspects, and does not imply that the illustrated process is preferred. Also, steps are generally described once per aspect, but this does not mean they must occur once, or that they may only occur once each time a process, method, or algorithm is carried out or executed. Some steps may be omitted in some aspects or some occurrences, or some steps may be executed more than once in a given aspect or occurrence.

When a single device or article is described herein, it will be readily apparent that more than one device or article may be used in place of a single device or article. Similarly, where more than one device or article is described herein, it will be readily apparent that a single device or article may be used in place of the more than one device or article. In this regard, descriptions herein of singular elements apply with equal force and effect to a plurality of the singular element and at least one of the singular element. Thus, the term "a," "an," "the" as used herein in connection with a singular apparatus or method step includes a plurality of the apparatus or method steps and at least one of the apparatus or method steps. Conversely, descriptions herein of plural elements apply with equal force to the singular element, or at least one of the singular element. Thus, a plural apparatus or method steps described herein includes the singular "a," "an," and "the," as well as "at least one."

The functionality or the features of a device may be alternatively embodied by one or more other devices that are not explicitly described as having such functionality or features. Thus, other aspects need not include the device itself.

Techniques and mechanisms described or referenced herein will sometimes be described in singular form for clarity. However, it should be appreciated that particular aspects may include multiple iterations of a technique or multiple instantiations of a mechanism unless noted otherwise. Process descriptions or blocks in figures should be understood as representing modules, segments, or portions of code which include one or more executable instructions for implementing specific logical functions or steps in the process. Alternate implementations are included within the scope of various aspects in which, for example, functions may be executed out of order from that shown or discussed, including substantially concurrently or in reverse order, depending on the functionality involved, as would be understood by those having ordinary skill in the art.

As described below, methods and apparatus are provided for dosing a food product or other substrate with a desired dosage of active pharmaceutical ingredient (API). In particular, as will be described in detail below, a dosing system can include a dosing machine having a dosing head that delivers microdroplets that contain the API to an underlying substrate, and an imaging system that is configured to image the microdroplets as they travel from the dosing head to the substrate.

Referring now to FIGS. 1A-2, all of the above method steps and apparatus described herein, including an active-containing substrate, can be incorporated into or provided by any suitable dosing system 20. While examples of dosing system 20 is illustrated and described herein, it is recognized that numerous alternatives are available for dispensing a dose of the active pharmaceutical ingredient onto or into a desired substrate as described above. In one example, the dosing system 20 is configured to deliver an active pharmaceutical ingredient 22 to a substrate 23, which can be configured as an edible product 24, thereby producing an active-containing substrate. When the substrate is an edible product, the active-containing substrate can be referred to as an active-containing edible product. As described above, the edible product 24 can be any suitable food product. Further, as described above, the active pharmaceutical ingredient can include at least one cannabinoid, at least one alternative drug or material that provides a health benefit or recreational drug experience, or any desired alternative ingestible controlled substance as designated by law. It will be appreciated that the dosing system 20 can provide a cost-effective and efficient method for providing a product line of substrates having desired amounts and types of active pharmaceutical ingredients.

In some instances, it may be desirable to add one or more auxiliary edible products to the prepared edible product 24, either before or after delivering the active pharmaceutical ingredient 22 to the edible product 24. Examples include adding icing to a cookie, or frosting to a brownie or cake. However, in these examples, the cookie and brownie can have been fully cooked or otherwise prepared prior to adding the pharmaceutical ingredient. The system 20 can include one or more up to all of a delivery station 28 that is configured to receive one or more edible products, a dosing station 36 configured to deliver an approximate dose of the active pharmaceutical ingredient (API) 22 to the one or more edible products, a post-processing station 40, and a packaging station 42 that can be configured to package the edible product 24 that carries the approximate dose of the active pharmaceutical ingredient 22. In some examples the approximate dose can be a precise dose as described herein. The post-processing station 40 can be configured to at least one of 1) dries a solvent, for instance, when the API is delivered as a solution, 2) changes, for instance increases, a viscosity of the API, 3) further adheres the API to the substrate, 4) disperses the API along the substrate, and 5) increases absorption or diffusion of the API into the substrate. Operation of the system can be controlled by any suitable controller, such as the Champion 3700 Digital Dispensing Benchtop System commercially available from Creative Automation Company, having a place of business in Sun Valley, CA.

The terms "substantial," "approximate, "about," and words of similar import when used with respect to a quantity, volume, mass, weight, dosage, size, shape, direction, or other parameter, include the stated parameter specifically along with ranges within plus and minus 20% of the stated parameter, for instance plus and minus 10% of the stated parameter, including within plus and minus 5% of the stated parameter, such as within plus and minus 2% of the stated parameter, including plus and minus 1% of the stated parameter.

When the at least one active pharmaceutical ingredient is to be delivered as an API-containing liquid 25, which can be a solution of the type described above or a pure API for instance as an oil, the dosing system 20 can include a holding tank 26 that is configured to retain the liquid 25. Thus, while the liquid 25 can be a pure cannabis extract in one example, in other examples the cannabis extract can be mixed or otherwise combined with one or more other materials as desired, such as a solvent. In one example, the liquid is a solution having an approximate concentration of the cannabinoid or other active pharmaceutical ingredient 22 described above. The approximate concentration of the active pharmaceutical ingredient in the API containing material can be a known concentration described above. Thus, the active pharmaceutical ingredient 22 can define the solute of the solution, and the solution can define any suitable solvent. In one example, the solvent can be an alcohol, such as ethanol or any alternative alcohol as desired, or any other viscosity reducing agent as desired. In one example, the liquid 25 can contain a concentration of the active pharmaceutical ingredient that is in a range from approximately 40% up to approximately 90%, such as from approximately 50% to approximately 70% by volume in solution with the solvent. It is recognized that the solvent will be removed substantially in its entirety during a subsequent drying step. For instance, the solvent can easily evaporate after being applied to the edible product 24. Nevertheless, it may be desired for the solvent to be safe for consumption in trace amounts.

Alternatively, the cannabinoid or other active API-containing liquid 25 can be a stand-alone extract, meaning that it is not mixed with a carrier that is designed to be burned or otherwise evaporated off. The extract can be purified, partially purified, or unpurified as desired. It is recognized that such stand-alone extracts can be in the form of a resin having a relatively high viscosity that can prevent the extract from being suitably free flowing for easy delivery to the substrate 23. Therefore, as described in more detail below, the dosing system 20 can include one or more heaters that are configured to raise the temperature of the extract, thereby lowering the viscosity of the API-containing liquid. Alternatively or additionally, an additive such as alcohol can be added to the liquid 25 that lowers the viscosity of the liquid. The alcohol readily evaporates after the liquid 25 has been applied to the substrate 23. It is recognized that the extract having a suitably low viscosity can be readily delivered to the substrate in any manner described herein. For instance, it can be desirable to maintain the extract at a heated temperature during application of the extract to the substrate 23. The heated temperature can range from about 100 degrees F. to about 200 degrees F., such as about 150 degrees F. to approximately 180 degrees F. Although it is envisioned that the extract has a sufficiently low viscosity at room temperature, it may nevertheless be desirable in some instances to maintain the solution at the heated temperature. Because the approximate dose of the at least one cannabinoid in the liquid 25 is known, a predetermined approximate volume of the liquid 25 delivered from the holding tank 26 to the dosing station 36, and thus to the edible idem 24, can contain approximately a predetermined approximate desired dose of the pharmaceutical ingredient 22.

A delivery station 28 can be configured to receive a plurality of substrates 23 such as a plurality of edible products 24. This, while the substrates are illustrated as edible products 24, it is recognized that the substrates can be configured as any suitable alternative substrate as described above. In one example, the dosing system 20 includes one or more support surfaces 30 of at least one support member 32 that are configured to receive and support a respective one or more edible products 24. The support surfaces 30 can be defined by respective predetermined locations of the support member 32. The predetermined locations can be defined by geometric markings. Alternatively or additionally, the predetermined locations can be defined by pockets 34 that are defined by the support member 32. At least one or both of the support member 32 and the dosing station 36 can be movable so as to bring the dosing station 36 into alignment with the edible product 24. The dosing station 36 can be configured to deliver the approximate volume of the liquid 25 to one edible food product at a time, or can be configured to deliver a plurality of approximate volumes of the liquid 25 to a respective plurality of edible food products simultaneously. The dosing station 36 can be configured as an ultra-low volume liquid handling machine commercially available from Biofluidix having a place of business in Freiburg, Germany.

In one example, the support member 32 can be configured as any suitable delivery member such as a conveyor 38 or other suitable support member that is designed to support and transport the edible products to be brought into operative alignment with the dosing station 36. The conveyor 38 can be movable so as to correspondingly transport the edible product 24 from the delivery station 28 to the dosing station 36. Alternatively, the support surface 30 can be stationary, and the dosing station 36, including the applicator which can be configured as one or more dosing heads as described below, can be movable to be brought into alignment with the substrate 23. Alternatively still, both the support surface 30 and the dosing station can be movable so as to bring the dosing heads into alignment with the substrate 23. Thus, it can be said that at least one of the support surface 30 and the dosing station 36 can be movable with respect to the other of the support surface 30 and the dosing station 36 so as to bring the substrate 23 into alignment with the dosing heads of the dosing station 36.

Alternatively still, it is recognized that the dosing system 20 can be configured for self-service whereby a user places the substrate onto the support surface 30 at the dosing station 36. Alternatively, the user can place the substrate 23 onto the support surface 30, and manually moves the substrate 23, for instance along the support surface 30, to the dosing station 36. In this example, the support surface 30 can be a stationary support surface. Further, the dosing station can be stationary.

After the active pharmaceutical ingredient has been delivered from the dosing station 36 to the substrate 23, the active-containing substrate 23 can be moved from the dosing station 36 to the post-processing station 40. The active-containing substrate 23 can be moved from the dosing station 36 to the post-processing station 40 using the support surface 30 or any suitable alternative apparatus. In this regard, the post-processing station 40 can be positioned inline with the dosing station 36 along the support surface 30 in some examples. Alternatively, the post-processing station 40 can be offline with respect to the support surface 30. Thus, the active-containing substrate can remain at the post-processing station 40 for as much time as desired until the active-containing substrate is suitable to be packaged. At that point, the active-containing substrate can be moved from the post-processing station 40 to the packaging station 42. The support surface 30 or any suitable alternative apparatus can move the active-containing substrate from the post-processing station to the packaging station 42. In this regard, the post-processing station 40 can be positioned inline with the dosing station 36 along the support surface 30, or can be offline with respect to the support surface 30.

Once the edible product 24 is aligned with the dosing station 36, the dosing station 36 is configured to deliver a predetermined approximate volume of the active pharmaceutical ingredient, such as at least one cannabinoid, to the edible product. In some examples, the active pharmaceutical ingredient can be presented as the liquid 25. Because the concentration of the active pharmaceutical ingredient in the liquid 25 is known, and the desired dose of the active pharmaceutical ingredient to be delivered to the substrate 23 is known, the approximate volume of the liquid 25 to be delivered to the substrate 23 can be determined. In some examples, electrostatic forces can be created that drive the active pharmaceutical ingredient to the substrate 23, whereby the active pharmaceutical ingredient and the substrate are oppositely charged. For instance, the substrate 23 can be provided with a negative electrical charge, and a positive charge can be applied to the liquid or powder to be delivered, thereby creating the electrostatic charge.

In other examples, it is recognized that the active pharmaceutical ingredient can be delivered to the substrate 23 as a powder. For instance, the liquid 25 containing the at least one cannabinoid can be in the initial form of a resin that can dry and crystallize. The resulting crystals can be ground into a powder having a desired dose of active pharmaceutical ingredient. Because the density of the active pharmaceutical ingredient in the powder is known, and the desired dose of the active pharmaceutical ingredient to be delivered to the substrate 23 is known, the approximate mass of the powder to be delivered to the substrate 23 by the dosing station 36 can be determined.

The dosing station 36 can include at least one applicator of the type described above, such as a plurality of applicators. Each applicator can define a dosing head 46 that is configured to dispense a respective approximate quantity of the approximate volume of the liquid 25 that is delivered from the holding tank 26. Thus, the dosing station 36 can include at least one dosing head 46 such as a plurality of dosing heads 46. The dosing station 36, and in particular the applicators and thus the dosing heads 46, is in fluid communication with the holding tank 26. Thus, the dosing heads 46 are configured to receive respective quantities of the volume of the liquid 25 delivered from the holding tank 26, and dispense the respective quantities to the edible product 24. The respective quantities dispensed by the dosing heads 46 cumulatively define the approximate volume of liquid 25 that has been received from the holding tank 26.

As will now be described, the dosing heads 46 can be configured to deliver accurate quantities of the volume of the liquid 25 to the edible products 24. In some examples, the accurate quantities can be microquantities applied to the edible product 24 in the form of droplets that can be sized as microdroplets, as described in more detail below. Thus, the edible products 24 can receive a predictable dosage of the active pharmaceutical ingredient. Further, the dosage of the active pharmaceutical ingredient can be applied at specific locations of the edible product as desired. For instance, in certain examples, it may be desirable to deliver the active pharmaceutical ingredient such that it is substantially evenly distributed on or in the edible product 24. As a result, for instance when the edible product is a large baked good, consumption of different regions of the edible product in equal volumes will cause ingestion of substantially identical quantities of the active pharmaceutical ingredient. One non-limiting example of a large baked good can be a brownie. Further, when the edible product 24 is a bite-size food product that is the product of batch ingredients that have been mixed and/or cooked and subsequently singulated, consumption of different bite-size food products having equal volumes will cause ingestion of substantially identical quantities of the active pharmaceutical ingredient. One non-limiting example of such a bite-sized food product can be a gummy candy. Bite sized food products are those that are designed to be fully consumed in a single bite, such as dried fruit and nuts and gummy candies. In one example, the dosing heads 46 can be defined by a True Volume™ Piston Positive Displacement Pump commercially available from Creative Automation Company having a place of business in Sun Valley, CA In another example, the dosing heads 46 can be defined by a Pipetman M P10M device commercially available from Gilson Inc., having a place of business in Middleton, WI.

Referring now to FIG. 2 in particular, the dosing station 36 can include an injection reservoir 49 disposed between the holding tank 26 and the dosing heads 46. The dosing station 36 can include a first conduit 51 that extends from the holding tank 26 to the reservoir 49, and a second conduit 53 that extends from the reservoir 49 toward the dosing heads 46. Thus, the reservoir 49 can receive the volume of the liquid 25 from the holding tank 26. The dosing station 36 can further include a second conduit 53 that extends from the reservoir 49. The second conduit 53 can extend to a manifold 55. The reservoir 49 can thus deliver the volume of the liquid 25 to the manifold 55 under a pressure differential provided by a pump, and the manifold 55 can distribute the volume of liquid 25 to the dosing heads 46. In this regard, it should be appreciated that the second conduit 53 is in fluid communication with the dosing heads 46. The pump can be a positive pump that defines a positive pressure differential. The holding tank 25 can put under positive pressure so as to provide a positive force that urges the liquid 25 out of the holding tank 26 toward the dosing heads 46. Alternatively, the holding tank 25 can put under negative pressure so as to draw the liquid 25 out of the holding tank 26 toward the dosing heads 46. In other examples, the dosing system 20 can include a plurality of pumps that are each configured to provide a respective pressure differential to a respective one or more of the dosing heads 46.

Each pump defines a piston that is movable in a cylinder along a stroke length at a stroke velocity to eject predetermined accurate volumes of the liquid 25 as successive microdroplets. Because the liquid 25 has a concentration of API, movement of the piston in the cylinder along the stroke length at the stroke velocity can eject a predetermined accurate quantity of API as successive microdroplets. When at least one or both of the stroke length and stroke velocity is decreased, the resulting size of the microdroplets can be decreased. Conversely, when at least one or both of the stroke length and stroke velocity is increased, the resulting size of the microdroplets can be increased. In one example, a plurality of pumps can include respective pistons that are movable in corresponding cylinders along respective stroke lengths to eject predetermined accurate volumes of the liquid 25 as successive microdroplets. In this regard, the stroke length of the piston that delivers the liquid 25 to a first at least one dosing head 46 can be different than the stroke length of the piston that delivers liquid 25 to a second at least one dosing head 46. Alternatively, the pumps can include an elastic micropipe with an inner diameter that is partially squeezed by a piezo stack actuator so as to drive the liquid 25 out of the dosing head 46.

In some examples, different dosing heads 46 can be configured to deliver different quantities of the respective volume of liquid 25 to the edible product 24 (see FIG. 1). Further, the liquid 25 delivered by the first at least one dosing head 46 can include a different active pharmaceutical agent than the liquid 25 delivered by the second at least one dosing head 46. Further still, the dosing system 20 can be configured to deliver any number of API-containing liquids 25 each containing a different pharmaceutical agent to a respective at least one dosing head 46. Accordingly, the dosing heads 46 can combine to deliver active pharmaceutical agents from different liquid extracts in different quantities onto a common substrate 23. Alternatively or additionally, the different liquids can have different concentrations of their respective active pharmaceutical agent. The dosing system 20 can therefore include any number of holding tanks 26 as desired, each tank containing a different liquid extract that contains a different at least one pharmaceutical active ingredient. The different liquid extracts can be delivered to different respective ones of the dosing heads 46. Thus, different dosing heads can be configured to deliver different cannabinoids to the substrate.

As one example, a first group of dosing heads 46 can be configured to deliver microdroplets having a dose of a first active pharmaceutical agent, and a second group of at least one dosing head 46 such as a plurality of dosing heads 46 can be configured to deliver second microdroplets having a dose of a second active pharmaceutical agent, wherein the second active pharmaceutical agent is different than the first active pharmaceutical agent. For instance, the first active pharmaceutical agent can be THC, and the second active pharmaceutical agent can be CBD. Further, the first active pharmaceutical agent can be delivered in a different predetermined approximate dose than the second active pharmaceutical agent. Further still, the tank containing the first active pharmaceutical agent can be maintained at a different temperature than the second tank. Thus, the viscosity of each of the respective API-containing liquids 25 can be individually controlled. Additionally, the temperature of one or more up to all of the respective conduits 51 and 53 and at the respective dosing heads 46 can be different so as to individually control the viscosity of each liquid extract as it travels from the respective tank to the respective one or more dosing heads 46. In other examples, the first group of dosing heads 46 can be configured to deliver microdroplets having a first dose of an active pharmaceutical agent, and the second group a plurality of dosing heads 46 can be configured to deliver second microdroplets having a second dose of the active pharmaceutical agent. The second dose can be less than the first dose in some examples.

The dosing system 20 can include any suitable feedback mechanism to provide an indication that the at least one dosing head 46 has delivered the at least one active pharmaceutical ingredient to the substrate 23. The feedback mechanism can be a closed feedback loop in some examples. For instance, a pressure sensor can be placed in the conduit 53 so as to measure the backpressure in the conduit 53. A drop in the backpressure, for instance, can indicate that the respective at least one dosing head 46 has delivered the respective at least one active pharmaceutical ingredient to the substrate 23. Alternatively, the dosing system 20 can include a load cell that determines, by sensing weight, that the substrate 23 is in alignment with the dosing head 46. Alternatively still, the dosing system 20 can include a visual recognition system that includes a visual sensor to visually identify that the substrate 23 is in alignment with the dosing head 46. It is therefore appreciated in some examples, that the substrates 23 can be positioned at any location on the support surface that need not be a predetermined location of the support surface.

Further, the dosing system 20 can include a camera that is designed to measure a quantification of the microdroplets delivered from the dosing heads 46. For instance, the camera can measure a cross-sectional dimension of the microdroplets as they travel from the dosing heads 46 to the substrate 23. It is recognized microdroplets can be elongated as they travel out of the dosing heads. However, the surface tension of the microdroplets can cause the microdroplets to become more spherical as they travel from the dosing heads 46 to the substrate. Thus, in one example, the cross-sectional dimension can be a maximum cross-sectional dimension that approximates the diameter of a sphere, such that an approximation of the volume of the microdroplets can be calculated if desired. However, the cross-sectional dimension can be any suitable alternative cross-sectional dimension that has a relationship to the volume of the microdroplet. The cross-sectional dimensions or calculated approximations of the volumes of the microdroplets can be compared to each other so as to ensure repeatability of the volume of microdroplets being delivered to the substrates 23, or to verify a desired variation in the volumes of microdroplets. The cross-sectional dimensions or calculated approximations can then be integrated into the feedback look to ensure proper operation of the dosing system 20. In one example, the camera can be a SmartDrop System commercially available from Biofluidix having a place of business in Freiburg, Germany.

As described above, the dosing system 20 can be configured to deliver heat to the liquid 25 either in one or more of the conduits and/or in the dosing head 46 prior to or during dispensing of the API containing liquid to the substrate 23. The heat can be sufficient to decrease the viscosity of the API-containing liquid 25. In some examples, for instance when the API-containing liquid 25 includes a solvent, the step of delivering heat to the liquid 25 can cause the solvent to evaporate, such that pure API having a sufficiently low viscosity is dispensed from the dosing heads 46. Thus, in one example, the API-containing liquid 25 can include the API and solvent, and can travel from the holding tank 26 to the dosing head 46. The API-containing liquid 25 can be heated between the holding tank 26 and the dosing head 46 to decrease the viscosity of the liquid 25 and, in some instances, evaporate some or all of the solvent. Alternatively or additionally, the API-containing liquid 25 can be heated at the dosing head 46 so as to decrease the viscosity of the liquid 25 and, in some instances, evaporate some or all of the solvent. In one example, the dosing system 20 can include at least one heater that delivers heat to one or more up to all of the first conduit 51, the second conduit 53, the injection reservoir 49, the manifold 55, and the dosing head 46, so as to decrease the viscosity of the API-containing liquid and, in some instances, evaporate the solvent. In one example, the liquid 25 can be maintained at a temperature in a range from approximately 100 degrees F. to approximately 200 degrees F., such as from approximately 140 degrees F. to approximately 200 degrees F., and in one example from approximately 150 degrees F. to approximately 180 degrees F. Alternatively, in some examples such as when the liquid 25 is a solution, the liquid 25 can be maintained at room temperature.

While the dosing heads 46 can be configured to deliver to the substrate 23 the liquid 25 that contains at least one active pharmaceutical ingredient in one example, the dosing heads 46 can alternatively be configured to deliver the at least one active pharmaceutical ingredient to the substrate 23 in the form of a solid or powder in the manner described herein with respect to the liquid 25. Thus, examples above of applying the active pharmaceutical ingredient in the form of a liquid can apply with equal force and effect to a powder including the at least one active pharmaceutical ingredient, unless otherwise indicated. Each dosing head 46 can be configured to deliver microdroplets of the API as described above. Thus, it should be appreciated the powder can be delivered to the substrate 23 as a microquantity. The powder can be stored in the holding tank 26, and can be directed through the first conduit 51 and the second conduit 53 to the dosing head 46, either directly or through the manifold 55. Thus, it can be said that a quantity of API containing material can be applied to the substrate 23. The API containing material can be in the form of a powder or a liquid. Thus, the API containing material can include a desired concentration of active pharmaceutical ingredient as described above. In other examples, the API containing material can include only the active pharmaceutical ingredient.

Further still, while each of the dosing head 46 can be configured to dispense the API-containing liquid 25 that has been received from the holding tank 26, it is recognized that the API-containing liquid 25 can be delivered using other methods. For instance, the dosing system 20 can include a first holding tank that contains the API in liquid or solid form, and a second holding tank that contains a solvent. The API and solvent can mix at the dosing station 36. For instance, the API and solvent can mix at the dosing head 46. In one example, the dosing head can include a first chamber that receives the API, and a second chamber that receives the solvent. The API and solvent can mix in the dosing head 46 to produce a solution having the predetermined concentration of API. The solution produced in the dosing head 46 can then be dispensed as one or more microdroplets in the manner described herein. In some examples, the concentration can be varied inside the dosing head 46. That is, the respective proportions of API and solvent that are mixed in the dosing head 46 can be varied. Further, the API or the solution can be mixed with at least one other ingestible modifier that is configured to modify at least one of flavor, one or more mechanical properties, or one or more aesthetics of the cannabis or hemp material. The mixing can occur in the dosing head 46 or at any other location as desired. For instance, the at least one other edible product can be mixed in the liquid 25 in the holding tank 26 in some examples.

Referring again to FIGS. 1A-2B, in one example, the dosing heads 46 can be arranged in an array 48 that includes at least one row 50 of dosing heads 46 and. The dosing heads 46 of each row 50 can be substantially equidistantly spaced along the respective row 50. Alternatively, the dosing heads 46 can be variably spaced along the respective row 50. The array 48 can further include a plurality of columns 52 that space the rows 50 from each other. Each of the array 48 of dosing heads 46 can deliver successive microdroplets along respective flow paths from the dosing head to the underlying substrate or substrates. The dosing heads 46 can be equidistantly spaced along the respective columns 52. Alternatively, the dosing heads 46 can be variably spaced along the respective columns 52. In one example, all of the dosing heads 46 can be configured to deliver the same at least one active pharmaceutical ingredient. Alternatively, as described above, different groups of the dosing heads 46 can be configured to deliver respective different active pharmaceutical ingredients. Each group can include at least one dosing head 46 up to a plurality of the dosing heads 46. Each group can be defined by a respective one or more of the rows 50. Alternatively, each group can be defined by a respective one of the columns.

Referring now to FIGS. 1A-3, the dosing heads 46 can be aligned with different respective locations of a dosing zone 54 the edible product 24. Accordingly, the dosing heads 46 can be positioned to deliver their respective quantities of the volume of liquid 25 to the different respective locations of the dosing zone 54. Further, the dosing system 20 can be configured to deactivate select dosing heads 46 that are out of alignment with the dosing zone 54 and thus do not receive respective portions of the volume of liquid 25, and activate select dosing heads 46 that are aligned with the dosing zone 54 and thus receive respective portions of the volume of liquid 25. In some examples, the dosing system 20 can include a sensor that identifies the dosing zone 54 of the edible product 24. The sensor can be a camera, a weight sensor that measures the weight of the substrate 23 on the support surface and determines the dosing zone based on the weight and/or size, or any suitable alternative sensor. The dosing zone 54 can be at least partially defined by an outer perimeter 56 of the edible product 24. For instance, the dosing zone 54 can be defined in its entirety by the outer perimeter 56 of the edible product 24. Thus, an entire outer surface of the edible product 24 can define the dosing zone 54. In some examples, the dosing zone 54 can be disposed inside the outer perimeter 56 in its entirety. For instance, the dosing zone 54 can be greater than half, for instance greater than 75%, of a footprint defined by the outer perimeter. Either way, it can be said that the dosing zone 54 can be a substantially predetermined location with respect to the outer perimeter 56 of the edible product 24. Thus, the dosing zone 54 can be consistent among a plurality of differently sized edible products 24, such as cookies or brownies that can have similar but non-identical sizes and shapes.

The dosing heads 46 can be spaced from each other as desired so as to deliver a desired distribution of the active pharmaceutical ingredient to the edible product 24 in the dosing zone 54. Alternatively, one or more dosing heads 46 can be movable so as to deliver the active pharmaceutical ingredient to multiple locations of the edible product 24. In one example, the dosing heads 46 are configured to deliver a substantially even distribution of the volume of liquid 25 to the edible product 24 in the dosing zone 54. For instance, the respective quantity of the volume of suspension dispensed by each of the dosing heads 46 or each plurality of dosing heads can be substantially equal to the respective quantity of suspension dispensed by the other dosing heads 46 or other pluralities of dosing heads 46.

In another example, the dosing system 20 can divide the dosing zone 54 into a plurality of subzones. Each subzone can be configured to receive a different at least one active pharmaceutical ingredient. Thus, a first group of at least one dosing head 46 can deliver a first at least one active pharmaceutical ingredient to a first one of the subzones, and a second group of at least one dosing head 46 can deliver a second at least one active pharmaceutical ingredient that is different than the first at least one active pharmaceutical ingredient to a second one of the subzones. Alternatively or additionally, the first group of at least one dosing head 46 can be configured to deliver a first dose of the first at least one active pharmaceutical ingredient, and the second group of at least one dosing head 46 can be configured to deliver a second dose of the second at least one active pharmaceutical ingredient that is different than the first dose. In still another example, the first and second groups of at least one dosing head 46 can be configured to deliver the same at least one active pharmaceutical ingredient, but in different doses. The active pharmaceutical ingredient can be substantially evenly distributed in each of the subzones.

In some examples, at least one dosing head 46 such as a plurality of dosing heads 46 can be movable along the substrate 23 so as to deliver the respective at least one active pharmaceutical ingredient at different locations of the edible product 24. Further, the dosing heads 46 can be configured to deliver different active pharmaceutical ingredients to the substrate 23. For instance, the dosing heads 46 can be configured to deliver different combinations of liquids and/ or powders. In one example, the dosing heads 46 can deliver to the substrate 23 a first liquid or powder that contains a first active pharmaceutical ingredient. Next, the dosing heads 46 can deliver to the substrate 23 a second active pharmaceutical ingredient that is different than the first active pharmaceutical ingredient. Next, the dosing heads 46 can deliver to the substrate 23 a third active pharmaceutical ingredient that is different from each of the first and second active pharmaceutical ingredients, and so forth until all desired active pharmaceutical ingredients have been delivered to the substrate 23.

When the dosing heads 46 are arranged in groups of dosing heads 46 that each deliver a respective different at least one active pharmaceutical ingredient, the different active pharmaceutical ingredients can be delivered to respective different locations of the substrate 20. For instance, the dosing heads 46 can remain stationary with respect to the substrate 23 as the active pharmaceutical ingredient is delivered to the substrate 23. Alternatively, the dosing heads 46 can be movable along the substrate 23, such that the combination of active pharmaceutical ingredients as delivered by different groups of at least one dosing head 46 can be delivered to the same respective location of the substrate 20. The heads 46 can be movable such that the dosing heads 46 can deliver the respective active pharmaceutical ingredient to different respective locations of the substrate 23 than the other dosing heads. The active pharmaceutical ingredients in the different respective locations can be substantially evenly distributed in at least one direction along to the substrate 23. For instance, the active pharmaceutical ingredient in the different locations can be substantially evenly distributed in two perpendicular directions along the substrate 23.

The substrate 23 includes an external surface that defines an inner surface 60 that faces the support surface 30, and an outer surface 58 that is opposite the inner surface 60. The dosing heads can deliver the active pharmaceutical ingredient to the outer surface 58 of the substrate 23. The edible product 24 defines a thickness that extends from the inner surface 60 to the outer surface 58. The delivered volume of active pharmaceutical ingredient can substantially remain on the outer surface 58. Delivering the volume of liquid to the outer surface 58 can expose the liquid to oral receptors, thereby increasing speed of ingestion of the active pharmaceutical ingredient. Alternatively or additionally, the delivered volume of liquid 25 can permeate through the outer surface 58 so as to impregnate at least a volume of a thickness of the edible product that extends from the outer surface 58 to the opposed inner surface 60. Alternatively still, the active pharmaceutical ingredient can be injected into the substrate 23 between the inner surface 60 and the outer surface 58. For example, at least 20% of the active pharmaceutical ingredient can be disposed in a middle 75% of the thickness. The middle 75% of the thickness can be equidistantly spaced from each of the inner surface 60 and the outer surface 58. For instance, at least 20% of the active pharmaceutical ingredient can be disposed in a middle 50% of the thickness. The middle 50% of the thickness can be equidistantly spaced from each of the inner surface 60 and the outer surface 58. In some examples, the distribution along the outer surface of the substrate 23 can be different than the distribution along the thickness of the substrate 23 from the outer surface to the inner surface.

Figures 2A, 2B, 2C, 3:
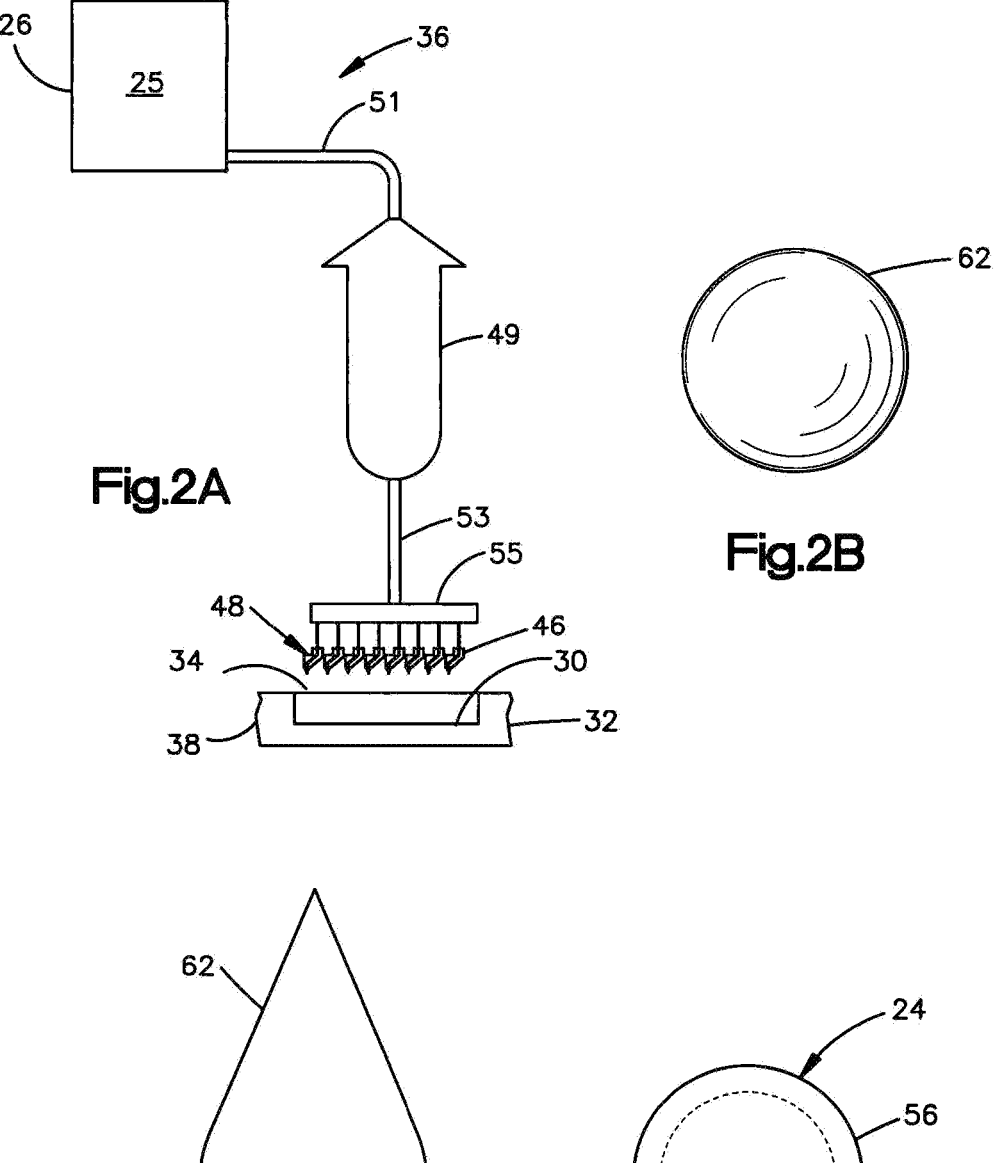
FIG. 2A is a schematic view of a dosing zone of the system illustrated in FIG. 1A.
FIG. 2B is a perspective view of a microdroplet in one example.
FIG. 2C is a side elevation view of a microdroplet in one example.
FIG. 3 is a plan view of the edible product illustrated in FIG. 1A, showing a delivery zone.

In one example, the dosing heads 46 can be configured to deliver the respective quantities of the active pharmaceutical ingredient to the respective locations of the outer surface 58 of the edible product 24 in the form of microdroplets 62. The microdroplets 62 can have any suitable size and shape as desired. In one example, the microdroplets 62 can including microquantities of the active pharmaceutical ingredient. For instance, the microdroplets 62 can define a maximum cross-sectional dimension along a horizontal direction that is in a range from approximately 5 millionths of an inch, for instance when printed, up to approximately 100 thousandths of an inch. For instance, the range can be from approximately 5 thousandths of an inch to approximately 50 thousandths of an inch. In one example, the maximum cross-sectional dimension along the select direction can be in a range from approximately 20 thousandths of an inch to approximately 40 thousandths of an inch. The dosing heads 46 are spaced from the edible products 24 along a direction of travel of the active pharmaceutical ingredient from the dosing heads 46 to the edible products 24. Thus, the active pharmaceutical ingredient is delivered to the substrate along the direction of travel. The select direction can be substantially perpendicular to the direction of travel. In one example, the dosing heads 46 are spaced above the edible products 24 along a vertical direction. Thus, the select direction can be a substantially horizontal direction. For instance, the dosing heads 46 can be spaced from the edible products 24 any suitable distance when delivering the active pharmaceutical ingredient to the edible products 24, such as from approximately 2 mm to approximately 25 mm. As shown at FIG. 2B, at least some of the microdroplets 62 up to all of the microdroplets 62 can be substantially spherical shaped. Alternatively or additionally, as shown at FIG. 2C, at least some of the microdroplets 62 up to all of the microdroplets 62 can be elongated, for instance substantially teardrop shaped or alternatively shaped as desired.

In one example, the microdroplets 62 are delivered from the dosing heads 46 to the respective locations of the edible product 24 under any suitable force, such as gravitational forces, electrostatic forces, or the like. In another example, the microdroplets 62 are delivered from the dosing heads 46 to the respective locations of the edible product under positive pressure. In this regard, the dosing station 36 can control whether the microdroplets 62 remain on the outer surface 58 of the edible product 24, and whether the microdroplets 62 permeate through the outer surface 58 into the thickness of the edible product 24 in the manner described above. In still other examples, one or more of the dosing heads 46 can be coupled to a respective needle that can be driven into the edible product 24 so as to deliver the respective quantity of the volume of liquid 25 into the edible product 24 at a location between the outer surface 58 and the inner surface 60. In some instances, the needle can be heated at a temperature suitable to soften or melt locations of the substrate contacted by the needle, in order to assist in the injection of the needle into the substrate. The heated needle can also maintain a desired viscosity of the at least one active pharmaceutical ingredient as the active pharmaceutical ingredient is being delivered through the needle and into the substrate. Whether the active pharmaceutical ingredient is delivered to the edible product 24 as microdroplets or as an injection, the active pharmaceutical ingredient can be delivered to the edible product in microquantities.

As described above, the dosing system 20 can include the post-processing station 40 that is configured to process the edible product 24 after the liquid 25 has been delivered to the edible product 24. The post-processing station 40 can be configured to dry the solvent, for instance, when the API is delivered as a solution. In this regard, the post-processing station 40 can include any suitable drying member, such as at least one drying head 70 or a plurality of drying heads 70 that are configured to deliver a drying agent to the respective locations of the edible product 24 so as to dry the liquid 25. It is appreciated that when the liquid 25 dries, the solvent of the delivered volume of liquid 25 that carries the active pharmaceutical ingredient also dries and can evaporate, leaving the active pharmaceutical ingredient on the substrate 23. In this regard, the drying heads 70 can be arranged in an array that has an equal number of rows and columns as the array of dosing heads 46. Further, the relative position of the drying heads 70 with respect to the other drying heads 70 can be the same as the relative position of the dosing heads 46 with respect to the other dosing heads 46. Thus, the drying heads 70 can be aligned with the active pharmaceutical ingredients that were delivered to the edible product 24 by the dosing heads 46.

The drying agent can be configured as any suitable light, including ultraviolet, laser, infrared, or the like. Alternatively, the drying agent can be a forced gas that is delivered to the outer surface of the edible product 24. The forced gas can be air, nitrogen, or any suitable alternative gas such as an inert gas. The forced gas can be heated, and can have a temperature that is in a range for instance from about 100 degrees F. to about 250 degrees F. Alternatively, the forced gas can be substantially unheated, and thus at ambient temperature. Alternatively still, the forced gas can be cooled, and thus at a temperature below ambient temperature. In this regard, the cooled forced gas can cause a cannabinoid to freeze on the surface of the substrate, or to delay evaporation of the solvent so as to allow the cannabis-containing solution to further impregnate the thickness of the substrate 23. Alternatively, the post-processing station 40 can expose the dosed substrate to ambient air or a controlled environment so as to dry the volume of liquid 25. It is recognized that the drying agent applied to the API can increase the viscosity of the API. The post-processing station can further cause the API to further adhere to the substrate 23. For instance, increasing the viscosity can cause the API to further adhere to the substrate 23. Further, applying forced air to the substrate 23 can cause the API to disperse along the substrate as the API travels along the outer surface of the substrate 23, thereby facilitating absorption of the API into the substrate 23. For instance, it is recognized that the API can become saturated in the portion of the substrate 23 that underlies the delivered microdroplets. Causing the API to move along the outer surface of the substrate 23 then allows the API to absorb into the substrate 23 at locations of the substrate 23 that are not saturated with the API. The post-processing station 40 can further cause the API to solidify on or in the substrate 23. In some examples, the API can crystallize on or in the substrate 23. Alternatively, the API can remain as an oil on or in the substrate 23. If the at least one cannabinoid is applied as a powder, the post-processing step can apply heat to the powder, thereby causing the at least one cannabinoid to liquify on the substrate 23. Subsequent cooling of the liquified powder can cause the liquid to solidify or crystallize or otherwise adhere on or in the substrate 23.

It is appreciated that energy can be applied to the substrate 23 to improve diffusion or absorption of the API into the substrate 23. For instance, when heat is applied to the surface of certain substrates 23, and in particular certain edible products, such as chocolate, baked goods, gummy candy, lollipop, and the like, the temperature of the surface of the edible product be raised to a level whereby the edible product melts, sweats, or otherwise assumes a form that is configured to encapsulate the API. The temperature can be increased, for instance, by directing at least one of heated forced air and a light to the surface.

Once the substrate 23 has been post-processed, the active-containing edible product 24 can be transferred from the post-processing station 40 to the packing station 42. At the packaging station 42, the dried edible products 24 can be individually wrapped in any suitable package 73. Alternatively or additionally, a plurality of the active-containing edible products 24 can be wrapped in a common package. The active-containing edible product 24 can include a cooked edible product, and a dose of an active pharmaceutical ingredient carried by the cooked edible product in the dosing zone of the cooked edible product. The dose of the active pharmaceutical ingredient can be substantially evenly distributed in the dosing zone. Because the edible product was fully cooked prior to adding the active pharmaceutical ingredient, the active pharmaceutical ingredient need not be cooked after the active pharmaceutical ingredient was added.

Figures 4A, 4B, 4C, 4D, 4E:
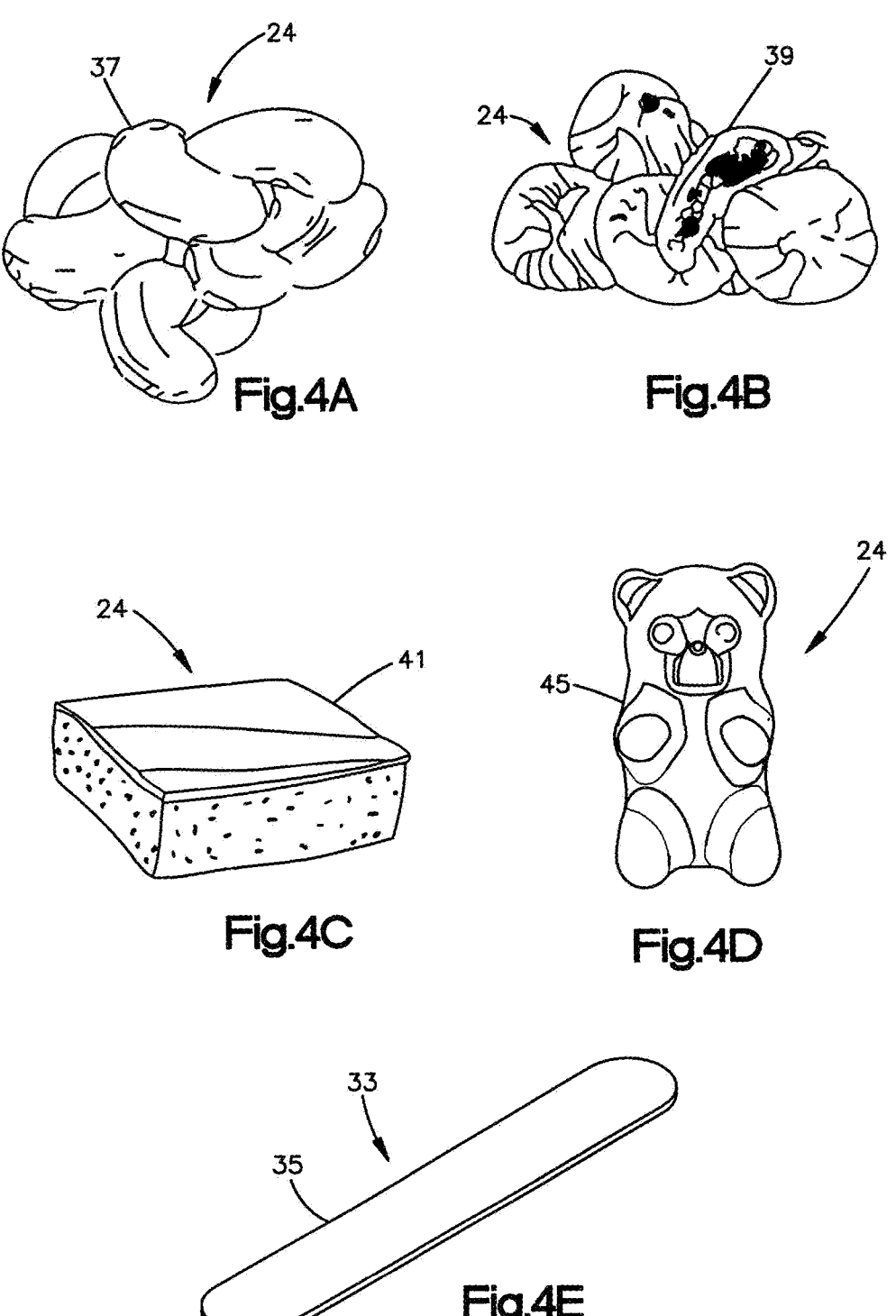
FIG. 4A is a perspective view of mixed nuts dosed with an active pharmaceutical ingredient in accordance with aspects of the present disclosure.
FIG. 4B is a perspective view of dried fruit dosed with an active pharmaceutical ingredient in accordance with aspects of the present disclosure.
FIG. 4C is a perspective view of a baked good dosed with an active pharmaceutical ingredient in accordance with aspects of the present disclosure.
FIG. 4D is a side elevation view of a gummy candy dosed with an active pharmaceutical ingredient in accordance with aspects of the present disclosure.
FIG. 4E is a perspective view of a tongue depressor dosed with an active pharmaceutical ingredient in accordance with aspects of the present disclosure.

In some examples, the edible product 24 can be configured as a plurality of nuts 37 (FIG. 4A) and/or fruits 39 (FIG. 4B) and/or a mixture of dried fruits and nuts and potentially other additional food product. It is appreciated that the API is not visible in FIGS. 4A-4E due to the nature of the figures. The active pharmaceutical ingredient can be applied to the nuts and fruits in any suitable manner as disclosed herein. In some examples, the nuts have been cooked, such as roasted. In other examples, the nuts can be raw. In some instances, the nuts or fruit can be prepared with salt, sugar, honey, or any suitable alternative ingredient. Thus, the nuts can be candied. In some examples, the fruit can be a raw fruit. In other examples, the fruit can be dried. In still other examples, the fruit can be candied. It is understood that fruits and nuts can have relatively low surface areas and volumes. Thus, variations in the dosage of active pharmaceutical ingredient applied to fruits and nuts can have a greater impact on the ratio of active pharmaceutical ingredient per volume of edible product when compared to edible products having larger surface areas and volumes.

Therefore, it can be particularly advantageous to accurately control the dosage of active pharmaceutical ingredient added to fruits and nuts. The active pharmaceutical ingredients can be applied to the fruits and nuts as microquantities in the manner described above, which allows for the accurate control of the dosage of active pharmaceutical ingredients applied to the fruits and nuts. Depending on the size of the fruit or nut, it is recognized that microdroplets having respective volumes ranging from approximately 5 nanoliters to approximately 20 microliters can be delivered to an individual fruit or nut. Thus, each fruit or nut can include a quantity or dosage of API in the range from approximately 2.5 micrograms to approximately 20 milligrams. Therefore, each microdroplet can contain a microquantity of API in a range from approximately 0.5 micrograms to approximately 1 milligram. It is recognized, of course, that the dosage of API per dried fruit or nut can vary as desired. For instance, other quantities of microdroplets can be delivered to fruits and nuts, for instance depending on the size of the fruit and nut, the size of the microdroplet, and the concentration of API in the microdroplet. The microquantity of API in a microdroplet can allow the dosage of API delivered to a substrate to be accurately controlled as described above. Further, the dosage of API per dried fruit or nut can be accurately controlled, as can a plurality of dried fruits and/or nuts that amount to a serving. For larger edible products, such as baked goods 41 (see FIG. 4C), the microdroplets can be applied in the range of approximately 5 nanoliters to approximately 20 microliters over the entire surface and greatly increase the total API delivered to the substrate to 100 milligrams or more.

It should be appreciated that several advantages can be achieved using the dosing system 20. In one example, the substrate 23 can include multiple active pharmaceutical ingredients, which can eliminate a conventional need to consume multiple medications each having a single active pharmaceutical ingredient. Further, microquantities of the active pharmaceutical ingredients can be applied to the substrate. Thus, the dosage of the at least one active pharmaceutical ingredient carried by the substrate can be better controlled with respect to conventional application processes. Further, the at least one active pharmaceutical ingredient can be distributed substantially evenly along the dosing zone. Further still, individual dosing of the active pharmaceutical ingredients on the substrate can allow for the use of locally produced active pharmaceutical ingredients that are applied after the substrate has been prepared, thereby avoiding the need to transport the applied active pharmaceutical ingredients across jurisdictional boundaries, which can be illegal in some jurisdictions or carry tax penalties. Further, dosing the substrate after the substrate has crossed the jurisdictional boundary can reduce or eliminate degradation of the active pharmaceutical ingredient during transportation across the jurisdictional boundary, which can sometimes involve long distances of transportation. In some examples, a dye can be used with the active pharmaceutical ingredient if desired, so as to confirm that the active pharmaceutical ingredient has been delivered to the substrate.

Figure 5A:
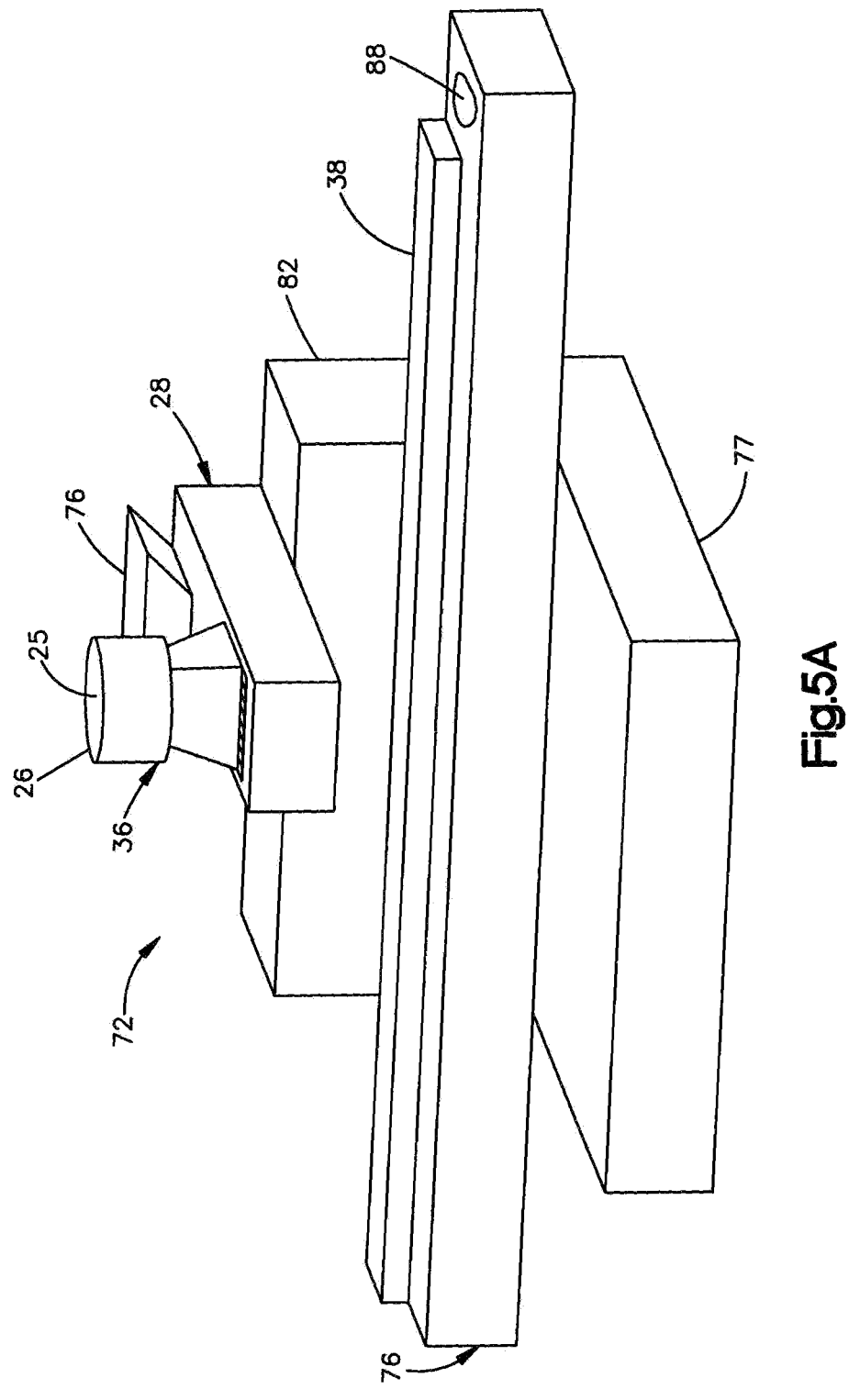
FIG. 5A is a perspective elevation view of a dosing machine constructed in accordance with one example.
Figure 5B:
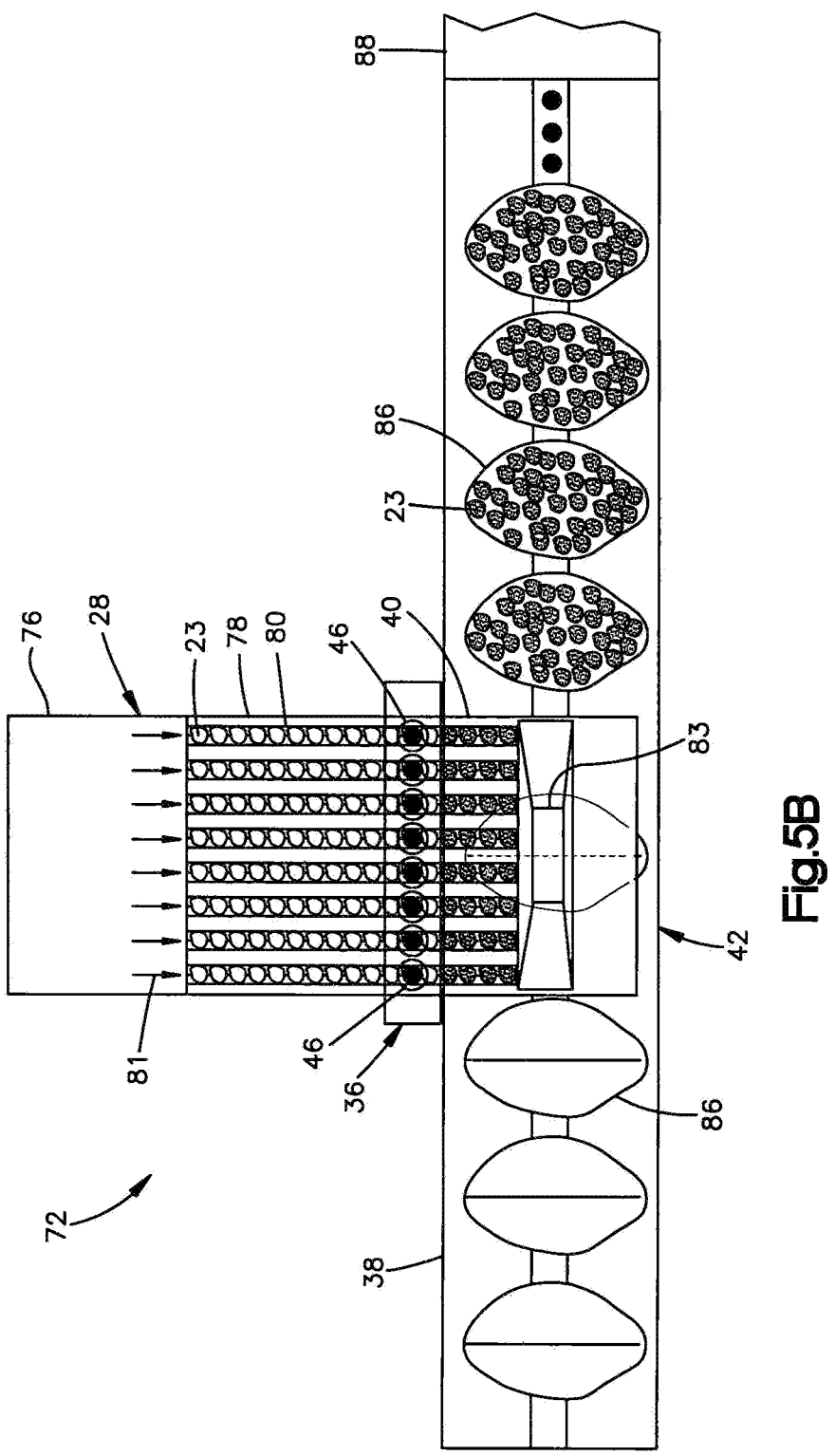
FIG. 5B is a schematic view of a method of dosing using the dosing machine illustrated in FIG. 5A.

Referring now to FIGS. 5A-5B, it is recognized that in some examples the dosing system 20 described above can be configured as a single unitary stand-alone dosing machine 72. The dosing machine 74 can include the conveyor 38, the holding tank 26, the delivery station 28, the dosing station 36, the post-processing station 40, and the packaging station 42. The dosing machine 74 can further include a support structure 76 that supports the conveyor 38, the holding tank 26, the delivery station 28, the dosing station 36, the post-processing station 40, and the packaging station 42. Thus, the conveyor 38, the holding tank 26, the delivery station 28, the dosing station 36, the post-processing station 40, and the packaging station 42 can be said to be integrated into the single stand-alone dosing machine, and supported by the common support structure 76. As will be further described in more detail below, the dosing machine 72 can further include a camera that measures the maximum cross-sectional dimension of the microdroplets. Further, the dosing system 20, and dosing machine 74, can include a cleaner that is configured to remove loose particulates from the substrate 23 prior to delivering the API to the substrate 23. For instance, in the case of salted nuts, loose salt can be removed from the nuts, while salt having strong adhesion to the nuts remain. In one example, the cleaner can be configured to deliver forced air to the substrate to remove loose debris from the substrate. Thus, when the API is delivered to the substrate, the API can have strong adhesion to the substrates 23. In some examples, the forced air can be heated so as to increase the temperature of the substrate so as to improve absorption or diffusion of the API into the substrate in the manner described herein.

The delivery station 28 can include a hopper 76 or other containment member that contains one or more of the substrates 23. The delivery station 28 can further include a delivery member 78 that is configured to receive the substrates from the hopper 76, and deliver the substrates 23 from the hopper 76 to the dosing station 36. For instance, the delivery member 78 can transport the substrates 23 from the hopper 76 to the dosing station 36, and further to a third location in alignment with a delivery location whereby the dosed substrates are delivered to the conveyor 38. The delivery member 78 can include define any suitable material that can have at least one elongated groove 80 or other suitable structure that directs the substrates 23 along a respective path 81 from the hopper 76 to the dosing station 36. For instance, the delivery member 78 can include a plurality of grooves 80 that define a plurality of paths 81 from the hopper 76 to a plurality of respective dosing stations 36. Alternatively, a plurality of delivery members 78 can define respective grooves 80 that extend along respective paths from the hopper 76 to the respective dosing stations 36.

In one example, the delivery member 78 can be downwardly sloped along a direction from a first location in alignment with the hopper 76 to a second location in alignment with the dosing station 36, and further to a third location in alignment with a delivery location whereby the dosed substrates are delivered to the conveyor 38. Further, the delivery member 78 can be configured to vibrate, shake, or otherwise cause the substrates 23 to travel along the delivery member 78 from the first location to the second location, and from the second location to the third location. Alternatively, the delivery member 78 can be configured as a conveyor so as to move the substrates 23 from the first location to the second location, and from the second location to the third location. Alternatively still, as noted above, a user can manually move the substrates 23 along the delivery member 78 or otherwise move the substrates to a position in alignment with the dosing station 36.

During operation, the substrates 23 loaded into the hopper 76. The substrates 23 are then delivered from the hopper 76 to the first location of the delivery member 78. The delivery can occur under gravitational forces or any suitable alternative structure and method. In particular, the substrates 23 can be delivered to the delivery member 78 such that they are arranged along their respective paths 81. The substrates 23 can be individualized and arranged in single file on their respective delivery members 78, and thus along their respective paths 81. Alternatively, groups of the substrates 23 can be arranged on one or more of the delivery members 78. The substrates 23 traveling along the respective paths 81 can define the same type of substrate, such as fruits or nuts, or a baked good or the like. Alternatively, the different types of substrates 23 can travel along the respective paths 81. For instance, the substrates 23 traveling along one path can include dried fruits. The substrates 23 traveling along another path or the same path can include nuts, either raw or roasted. The substrates 23 traveling along still another path can include a baked good.

The substrates 23 travel along the delivery member 78 to the second location, whereby the substrates 23 are aligned with the respective a least one dosing station 36. The dosing machine 72 can include a plurality of dosing stations 36, whereby each of the dosing stations 36 is aligned with a respective one of the delivery members 78. As described above, each of the delivery members 78 causes extends along a respective path 81. Thus, each of the dosing stations 36 is aligned with one of the respective paths 81, and is configured to deliver API to the substrates 23 that travel along the respective paths 81. In one example, the substrates 23 can be arranged on the delivery member 78 such that one or more dosing heads 46 of the dosing stations 36 aligned with the respective paths are configured to deliver API to only a single substrate 23 at a time as the substrates 23 travel along the respective paths 81. In particular, the dosing heads 46 can be configured to deliver microdroplets to each individual substrate 23 in the manner described herein. Because the API is delivered in microdroplets, an accurate predetermined dosage of API is delivered to each of the substrates 23.

In one example, the same API-containing liquid can be delivered to a plurality of the substrates 23. Alternatively, API-containing liquids having different API characteristics can be delivered to different substrates 23. The different substrates 23 can define respective pluralities of substrates. The pluralities of substrates can travel along different respective paths 81 to different dosing stations 36 that are operably aligned with the respective paths 81. The dosing stations 36 can deliver respective APIs to the aligned substrates 23, either individually or as a group of substrates 23, where the respective APIs have at least one API characteristic that is different than the other. Alternatively, the pluralities of substrates 23 can travel along the same path 81 to the same dosing station 36. Alternatively still, the pluralities of substrates 23 can travel along different paths 81 to the same dosing station 36. The same dosing station can deliver a first API-containing liquid to a first at least one substrate 23, such as a first plurality of substrates 23. The same dosing station can deliver a second API-containing liquid to a second at least one substrate 23, such as a second plurality of substrates 23. The first and second APIs can have at least one API characteristic that is different from each other. The different API characteristic can include at least one of 1) a concentration of the API, 2) a volume of API delivered to the substrates during the delivering step, which can include at least one of a different number of microdroplets and microdroplets having different volumes, 3) a composition of the API, 4) a modifier mixed with the API, the modifier configured to modify at least one of a flavor, a mechanical property, and an aesthetics of the delivered API, and 5) a location of at least one dosing zone of the substrate 23 that defines a location of the substrate 23 where the API-containing liquid is to be deposited. The mechanical property can include viscosity of the API-containing liquid in some examples. The mechanical property can further include the surface tension of the API-containing liquid that is delivered from the dosing station. It is further appreciated that the different API characteristic can include a different predetermined dosage that is delivered to the different substrates 23. In one example, the dosage can be predetermined to correspond to a dosing regimen over a period of time. Thus, groups of one or more substrates can have dosages that differ and are designed to be consumed at predetermined times over the course of the dosing regimen. For instance, the dosage can decrease over the period of time defined by the dosing regimen. Alternatively, each substrate 23 can receive API-containing liquid 25 having the same API characteristics. Further, different groups of substrates can receive API-containing liquid 25 with at least one different API characteristic, wherein all substrates among each group receive the same API-containing liquid 25.

Alternatively, it is envisioned that a predetermined quantity of substrates 23, or a plurality of substrates 23, such as dried fruits and/or nuts, can be grouped together on the delivery member 78 along the respective path 81. Thus, the dosing stations 36 can be aligned with the plurality of substrates 23 of the group. The dosing heads 46 can thus deliver a predetermined or target quantity of API-containing microdroplets to the group as a whole as opposed to each individual dried fruit or nut. Because the API is delivered in microdroplets, an accurate predetermined dosage of API is delivered to the group of substrates 23. The group of substrates 23 can be intended to be ingested in a single serving. Thus, the accurate predetermined dosage is ingested when the substrates 23 of the group are ingested. It is recognized that the predetermined quantity of substrates 23 dosed in a group are not limited to fruits and nuts, but to any type of edible product 24 that is designed to be consumed in quantities, such as chips, popcorn, pretzels, candies such as gummy candy 45 (FIG. 4D), and the like. It should therefore be appreciated that the dosing station can be configured to deliver an API to at least one substrate 23 at a time, which can include the single substrate 23 or the group of substrates 23.

Each dosing station 36 can include at least one dosing head 46, such as an array of dosing heads 46, and one or more holding tanks 26 that can contain a respective API-containing liquid 25 described above. It is recognized that a plurality of dosing stations 36 can receive the API-containing liquid 25 from a common one of the holding tanks. Alternatively, the dosing stations 36 can receive API-containing liquid 25 from a different holding tank 26. The API-containing liquids 25 in the different holding tanks 26 can have different APIs from each other or the same API. Thus, the API can be a cannabinoid or any suitable alternative active pharmaceutical ingredient. Each at least one dosing head 46 of the dosing station 36 can be operatively aligned with a respective one of the paths 81 so as to deliver the active pharmaceutical ingredient to the at least one substrate 23 traveling along the respective one of the paths 81. Accordingly, as the at least one substrate 23 travels to the second location along the respective path, the dosing station 36 delivers a predetermined quantity of the API-containing liquid 25 from the at least one dosing head 46 to the respective aligned at least one substrate 23. The dosing head 46 discontinues delivery of the API-containing liquid 25 when the at least one substrate 23 has received the predetermined quantity of the liquid 25. The dosing heads 46 of the array of dosing heads 46 can combine to deliver the predetermined quantity of the liquid 25 to respective different locations of the at least one substrate 23. That is, the locations of the at least one substrate 23 can be aligned with different dosing heads 46 of the array of dosing heads 46 that are aligned with the respective path 81.

After each at least one substrate 23 has received the predetermined quantity of liquid 25, the substrates 23 move along the delivery member 78 past the second location. The dosing stations 36 resume delivery of the liquid 25 when another at least one substrate 23 has traveled to the second location to a location in alignment with the at least one dosing head 46. In this regard, the at least one substrate 23 arranged sequentially along each respective paths 81 receive the predetermined quantity of liquid 25 from the aligned one of the dosing stations 36. The predetermined quantity can be equal to each other or different than each other as desired, depending on the at least one substrate 23 and the desired dosage of the active pharmaceutical ingredient that is to be delivered to the at least one substrate 23. The dosing machine 72 can include a processor 102 (see FIG. 6) programmed with the dosage quantities that are to be applied to the substrates 23 traveling along the at least one delivery member 78. The processor 102 can control the operation of the dosing station 36 and thus each of the dosing heads 46 described above. For instance, the dosing station 36 can include any suitable apparatus or sensor as to identify when one of the substrates 23 has traveled into alignment with the dosing head 46, and when no substrates 23 are aligned with the dosing head 46 that require delivery of liquid 25, and communicate the alignment information to the processor 102. The processor 102 then controls operation of the dosing heads 46.

Once the substrates 23 have been dosed with the active pharmaceutical ingredient-containing liquid 25, the substrates 23 travel along the delivery member 78 to the third location whereby they are delivered to the conveyor 38. In this regard, the delivery member 78 can be disposed in a spatial relationship with respect to the conveyor, such that the substrates 23 can travel from the delivery member 78 to the conveyor 38. In one example, the delivery member 78 is supported by a delivery support member 82 of the dosing machine 72. Thus, the support structure 76 can include a base 77 that supports the conveyor 38 and packaging station 42, and the delivery support member 82 that supports the delivery member 78 in addition to the dosing station 36, at least one holding tank 26, the at least one hopper 76, and the post-processing station 40. The substrates 23 can be dried as they travel from the second location to the third location. Thus, the dosing machine 72 can include a post-processing station 40 between the second location and the third location. The post-processing station can be configured as described above. Thus, once the substrate 23 is processed during the processing step, the API can adhere to the substrate 23.

The delivery support member 82 can support the delivery member 78 at a location above the conveyor 38, such that the dosed substrates 23 can travel from the support structure 78 down toward the conveyor 38. In one example, the dosed substrates 23 can travel under gravitational forces from the support structure 78 toward the conveyor 38. For instance, the delivery member 78 can transport the substrates 23 to the third location defined by an opening 83 in the delivery support member 82. Thus, the substrates 23 can travel through the opening 83 toward the conveyor 38. Alternatively, the third location can be configured as a conveyor or other suitable transport member that is configured to transport the substrates 23 toward the conveyor. The third location can be configured as a single opening or conveyor that receives the dosed substrates 23 from all paths 81 or a plurality of the paths 81. Alternatively, each path 81 can have its own dedicated third location.

The dosing machine 72 can include packaging station 42 that delivers a plurality of packages 86 to the conveyor 38. In one example, the packages 86 are placed onto the conveyor 38 upstream of the third location. The dosing machine 72 can include a reservoir that contains a plurality of packages, and can further deliver the packages sequentially onto the conveyor 38. Alternatively, a separate machine can deliver the packages to the conveyor 38. The conveyor 38 causes the packages 86 to move to a position in alignment with a respective one of the third locations. Thus, at least one of the substrates 23 that travels from the delivery member 78 toward the conveyor 38 is delivered into a respective package 86. It is contemplated that in some examples, a single dosed substrate, such as a baked good, will be delivered into each package 86. In other examples, it is contemplated that a plurality of dosed substrates, such as dried fruits and/or nuts, will be delivered into each package 82. For instance, a plurality of the substrates 23 can be delivered from a plurality of the paths 81 up to all of the paths 81 to a single respective container 82. Alternatively, one or more conveyors 38 can deliver the packages to respective locations whereby the packages 82 receive the respective at least one substrate 23 from the respective one of the plurality of paths 81 via the dedicated third location. Thus, packages 86 can thus simultaneously receive the respective at least one substrate 23.

The packaging station 42 can further include a sealing station 88 that is configured to enclose the packages 86 after they have received the respective at least one substrate 23. In particular, the conveyor 38 delivers the packages 86 to the sealing station 88 after they have received the respective at least one substrate 23. The sealing station can seal the package 86 and cause the package 86 to adhere to itself, for instance if the package 86 is a plastic bag or alternatively configured plastic package. The sealing station 88 can alternatively deliver and tighten a cap onto the package 86 if, for instance, the package is configured as ajar or other suitably configured package. The sealed package can then be delivered to a customer.

Figures 6, 7, 8A:
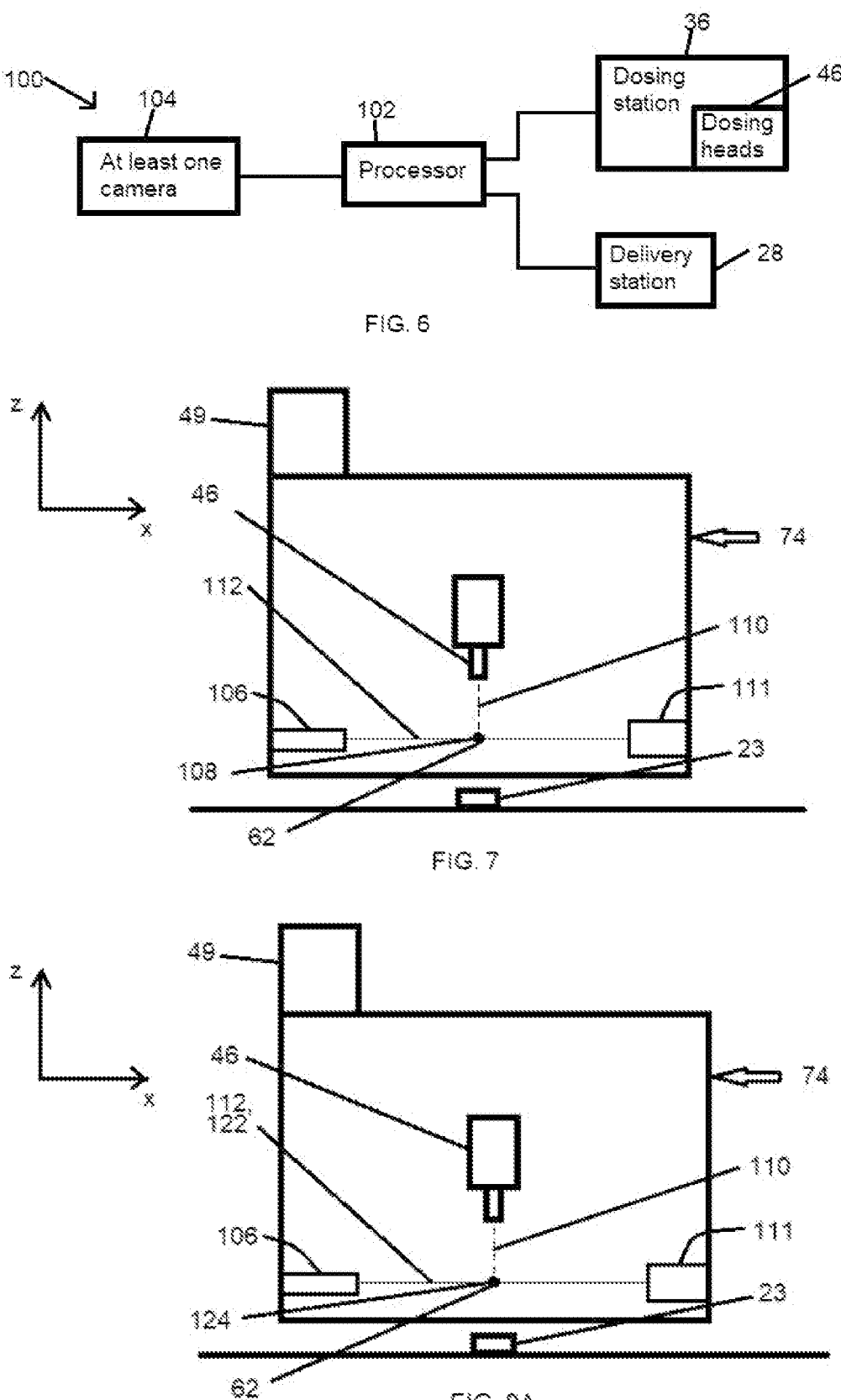
FIG. 6 is a schematic view of a control system in one example.
FIG. 7 is a schematic front elevation view of a dosing machine incorporating the control system in one example.
FIG. 8A is a schematic front elevation view of a dosing machine incorporating the control system in another example.

Referring now to FIG. 6, the dosing system 20 can further include a control system 100 that is configured to image the successfully delivered microdroplets along the flow path as they travel from the dosing head to the underlying substrate. It should be appreciated that the term "image" as used herein does not require an actual image of the microdroplets to be generated, but rather reflects the use of an imaging apparatus that is positioned to capture at least one property of the microdroplets as they travel along the flow path from the dosing head to the underlying substrate. In particular, the control system 100 can include at least one detector, which can be configured as at least one camera 104, that is configured to capture at least one image of the microdroplets. The control system 100 can include a processor 102 that is in communication with the at least one camera 104 and is configured to receive the images from the at least one camera 104. The processor 102 can send control signals to either or both of the dosing station 36 including the dosing heads 46 depending on the properties captured by the at least one camera 104. While the control system 100 can include a single processor 102 that receives signals from each at least one camera 104, it should be appreciated that the control system 100 can alternatively include multiple processors that receive signals from respective cameras, or that can be integrated into the respective cameras.

As will be described in more detail below, in one example the at least one camera 104 can detect edge boundaries of each microdroplet as it travels along the flow path from the dosing head to the substrate. Alternatively or additionally, the at least one camera 104 is configured to detect an optical property, such as fluorescence, of each microdroplet as it travels along the flow path from the dosing head to the substrate. Alternatively or additionally still, the at least one camera 104 is configured to capture a Raman scattering of light that travels through each microdroplet as it travels along the flow path from the dosing head to the substrate. The Raman scattering can be a Resonance Raman scattering or a Non-resonance Raman scattering. It should be appreciated further that any camera of the at least one camera 104 can detect the presence of each microdroplet along the flow path as they travel successively from the dosing head to a common substrate. Thus, the total quantity of microdroplets that have been delivered to each common substrate can be determined. Thus, the property of the microdroplets that are imaged can include at least one or more up to all of a size of the microdroplet, a light scattering property of the microdroplet, a fluorescence of the microdroplet, one or more edge boundaries of the microdroplet, and the presence of the microdroplet in the flow path. Each camera will now be described in more detail.

Figures 8B, 8C:
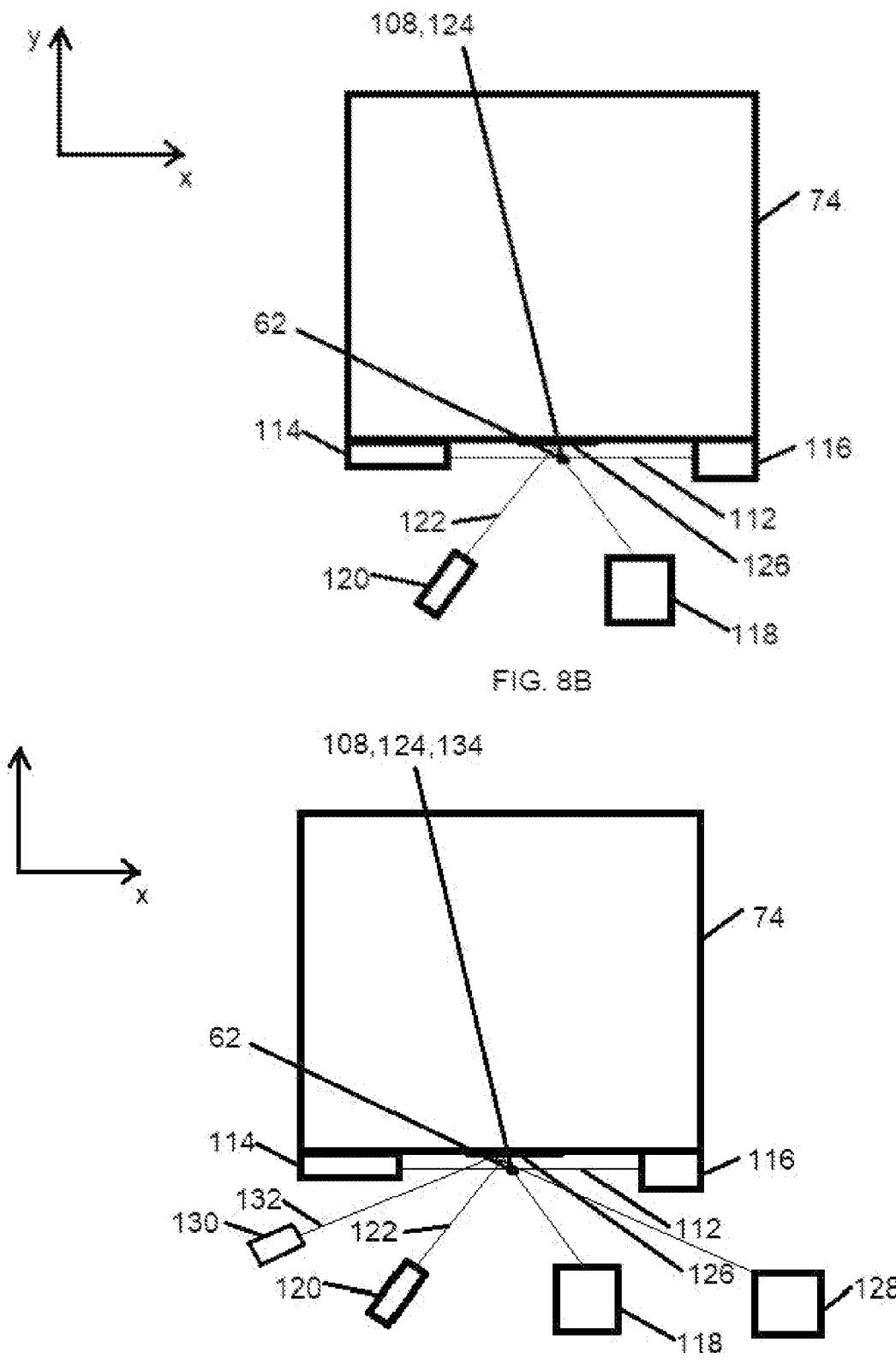
FIG. 8B is schematic top plan view of the dosing machine illustrated in FIG. 8A, shown with the dosing head removed for illustrative purposes.
FIG. 8C is another schematic top plan view of the dosing machine illustrated in FIG. 8B, incorporating the control system in yet another example.

Referring now to FIGS. 7-8C, the cameras of the control system 100 will now be described in one example. With reference to FIG. 7, the at least one camera 104 can include a first detector or camera 111 that is configured to measure a size of the microdroplets. The first camera 111 can be focused on a respective first location 108 of the flow path 110 so as to capture an image of the microdroplets as they travel along the flow path from the dosing head 46 to the underlying substrate. The first camera 111 can then capture the image of the microdroplets as they travel past the location. The first camera 111 can communicate with the processor 102 to identify each microdroplet as it travels along the flow path. In this regard, the processor 102 can count the number of microdroplets that are being delivered to each underlying substrate. The first camera 111, and all cameras described herein, can image the microdroplets along an imaging trajectory that intersects a respective location of the respective flow path. In one example, the imaging trajectory is substantially perpendicular to the flow path. In other examples, the trajectory can define an oblique angle relative to the flow path.

Further, the first camera 111 can detect the edge boundaries of each microdroplet as the microdroplets travel along the flow path. In some examples, the control system 100 can include a first light source 106 that directs a first beam of light 112 to the respective first location 108 of the flow path 110. The first beam of light 112 therefore illuminates each microdroplet in the flow path as it passes through the first location 108. In one example, the first light source 106 can be a light emitting diode (LED) that is directed through one or more filters to achieve uniform illumination in the first beam of light 112. In one example, the first beam of light 112 can be a white light beam. The first beam of light 112 can provide uniform light intensity at the respective first location 108 through which the drops are falling. In one example, the first location 108 can lie in a plane that is oriented perpendicular to the flow path, and the first beam of light 112 can travel along the plane through the first location 108. The first camera 111 can therefore be configured as a detector that detects the edges of each microdroplet.

The edges can be communicated to the processor that calculates the volume of each microdroplet. As described above, the microdroplets can be elongate as they travel out of the dosing head. However, the surface tension of the microdroplets can cause the microdroplets to become more spherical as they travel from the dosing heads 46 to the substrate. Thus, in one example, the cross-sectional dimension can be a maximum cross-sectional dimension that approximates the diameter of a sphere, such that the volume of the microdroplets can be calculated if desired. In particular, a maximum distance between outermost opposed edges of the microdroplets can be used to calculate the volume of a sphere having the maximum distance as its diameter. As successive microdroplets are delivered to a common underlying substrate, the processor 102 can determine or calculate the total cumulative volume of liquid that is delivered to the substrate by adding the respective volumes of the microdroplets delivered to the substrate. Based on the known concentration of API in the liquid, and thus in each microdroplet, and the volume of the liquid delivered to the underlying substrate, the processor 102 can determine or calculate the total quantity of API delivered to the substrate. Alternatively, as described in more detail below, the at least one camera 104 of FIG. 6 can include a camera that provides image data of the API in each microdroplet that allows the processor 102 to determine the volume of API in each microdroplet based at least in part on the image data of the API.

In some examples, the processor 102 can compare an actual size of the microdroplets determined as described above to a predetermined size. The processor 102 can adjust an operational parameter that changes respective sizes of the microdroplets when the actual size is outside of a tolerance from the predetermined size. In one example, the size can be a volume as described above. In another example, the size can be the maximum distance between the opposed outermost edges. When the actual size is greater than the predetermined size outside of the tolerance, the processor 102 can cause at least one or both of the stroke length and stroke velocity of the pump to decrease, thereby decreasing the actual size. When the actual size is less than the predetermined size outside of the tolerance, the processor 102 can cause at least one or both of the stroke length and stroke velocity of the pump to increase, thereby increasing the actual size. Alternatively or additionally, a parameter other than the stroke length and stroke velocity of the pump can be employed to change, for instance decrease, the microdroplet size. Similarly, the processor 102 can compare an actual quantity of cannabis in each of the microdroplets to a predetermined quantity of API that is to be included in each of the microdroplets. The processor 102 can adjust an operational parameter that changes the amount of API being delivered in each microdroplet. For instance, when the actual quantity of API in the microdroplets is greater than the predetermined quantity of API in the microdroplets outside of the tolerance, the processor 102 can cause at least one or both of the stroke length and stroke velocity of the pump to decrease, thereby decreasing the actual volume of the microdroplet which can thereby decrease the quantity of API in the microdroplets. When the actual quantity of API in the microdroplets is less than the predetermined quantity of API in the microdroplets outside of the tolerance, the processor 102 can cause at least one or both of the stroke length and stroke velocity of the pump to increase, thereby increasing the actual size which can thereby increase the quantity of API in the microdroplets. When the stroke length stroke velocity of the pump, or a parameter other than the stroke length and stroke velocity of the pump, is varied from a respective initial parameter value to a respective final parameter value to change the microdroplet size, the processor 102 can execute a routine to impart a substantially "S" shaped transition from the initial parameter value to the final parameter value thereby improving performance by minimizing transient instability in the microdroplet size.

Figure 9:
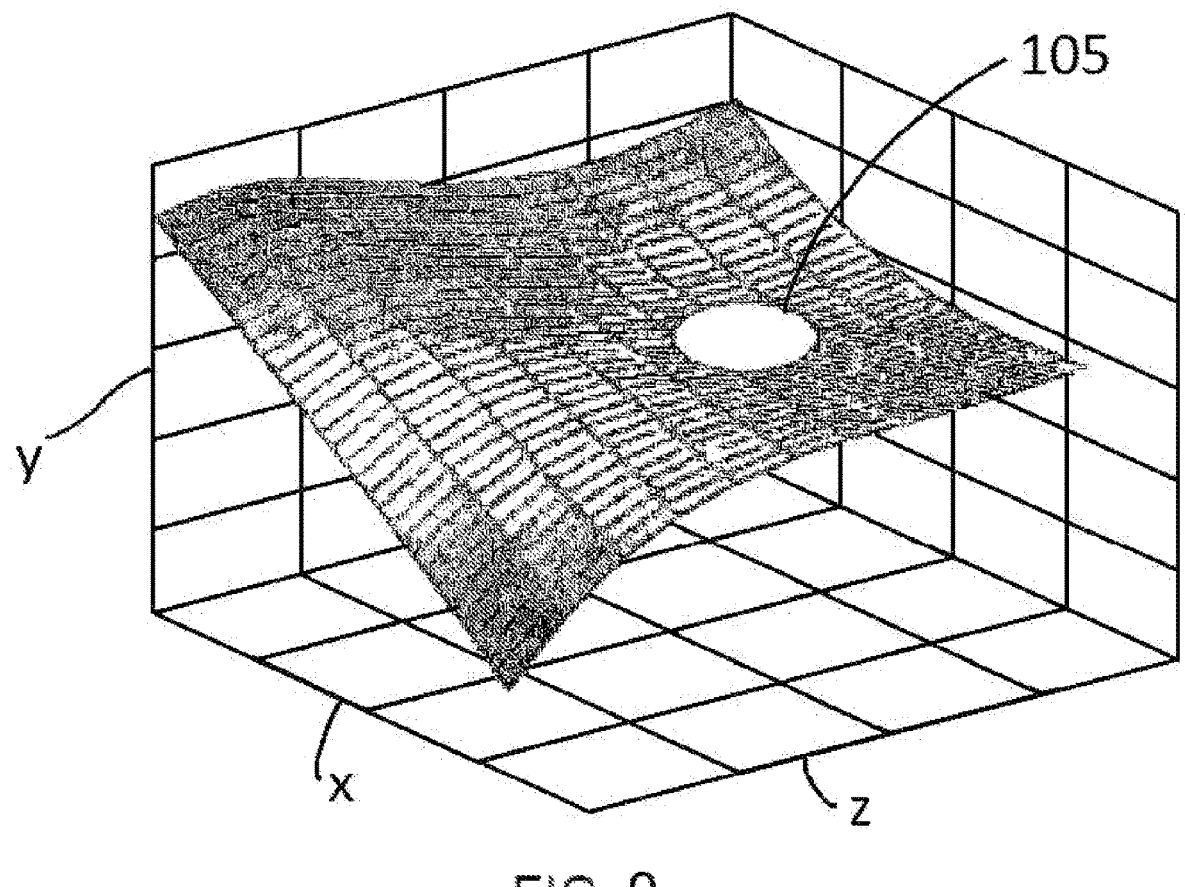
FIG. 9 is a plot illustrating a zone of stability in one example.

It is recognized that numerous parameters can affect the size of the microdroplets that are generated and delivered to the substrate. Some parameters can have a greater impact than others on the size of the microdroplets. In one example, the processor 102 can maintain respective a select group of parameters at settings that are determined to have reduced effects on the size of the microdroplets delivered from the dosing heads when those settings are adjusted when compared to the effects of adjustment of the settings when not included in the group of parameters. As illustrated at FIG. 9, whereby the x and z axes can define parameters in the select group of parameters, and the y axis is the size of the microdroplets, the generated curve defines a zone of stability 105 whereby adjustments of the x and z axes have a reduced impact on the y-axis as opposed to other locations on the curve.

Referring again to FIGS. 6-7, and as will now be described, based on the images taken by the first camera 111 of the microdroplets delivered to the substrate, the control system 100 can determine an actual total volume of the liquid that has been delivered to each substrate. The processor 102 can compare the actual total volume of liquid that has been delivered to the substrate to the predetermined volume of liquid to be delivered to the substrate. As will be appreciated from the description below, the control system 100, and in particular the processor 102, can cause the step of delivering the microdroplets to the substrate to stop once the actual total volume is within approximately 10% of the predetermined volume of liquid. That is, the processor 102 can prevent the liquid from traveling from the reservoir out the dosing head. In one example, the actual total volume can be within approximately 5% of the predetermined volume of liquid. For instance, the actual total volume can be within approximately 1% of the predetermined volume of liquid.

It is appreciated that the desired quantity of API to be delivered to the substrates can be predetermined prior to delivery of the microdroplets. Thus also, the volume of the liquid to be delivered to the substrates can be predetermined prior to delivery of the microdroplets, based on the known concentration of API in the liquid and the desired dosage of API that is to be applied to each substrate. The processor 102 can continue delivering microdroplets to each substrate until the processor 102 determines that an immediately subsequent microdroplet will cause the total quantity of API delivered to the substrate to exceed the predetermined quantity of API to be delivered to the substrate, or that an immediately subsequent microdroplet will cause the total volume of liquid delivered to the substrate to exceed the predetermined volume. An immediately subsequent microdroplet means that no additional microdroplets are delivered between the most recently delivered microdroplet and the microdroplet.

In one example, the processor 102 can cause the single immediately subsequent microdroplet to be delivered when the delivery of the single immediately subsequent microdroplet will cause the total quantity of API or total volume of liquid that is delivered to the underlying substrate to be closer to the predetermined quantity of API or the predetermined volume of liquid, respectively, as compared to discontinuing the delivery of microdroplets to the substrate prior to the delivery of the single immediately subsequent microdroplet. This process can be continued until the processor 102 determines that the delivery of the immediately subsequent microdroplet to the substrate will cause the total quantity of API or the total volume of liquid to be further from the predetermined quantity of API or the predetermined volume of liquid, respectively, as compared to discontinuing the delivery of microdroplets to the substrate prior to the delivery of the immediately subsequent microdroplet. At this point, the processor 102 can discontinue the delivery of microdroplets to the substrate, and can instead cause the microdroplets to be delivered to a subsequent substrate.

In other examples, once the processor 102 determines that the delivery of the immediately subsequent microdroplet will cause the total quantity of API delivered to the substrate to exceed the predetermined quantity of API, or that the delivery of the immediately subsequent microdroplet will cause the total volume of liquid delivered to the substrate to exceed the predetermined volume, the processor 102 can discontinue the delivery of microdroplets to the substrate, and can instead deliver microdroplets to a subsequent substrate. Alternatively, the processor 102 can discontinue the delivery of microdroplets immediately after delivering the immediately subsequent microdroplet when the total volume of liquid, or the total quantity of API, delivered to the substrate is greater than the predetermined volume of liquid or predetermined quantity of API, respectively. The term "immediately after" in this context means that no further microdroplets are delivered. In other examples, the processor 102 can discontinue the delivery of microdroplets to the substrate when the current quantity of API or total volume of liquid delivered to the substrate is less than the predetermined amount of the desired quantity of API or predetermined total volume of liquid to be delivered to the substrate by a desired value.

In still other examples, the processor 102 can compare a current difference between total quantity of API or volume of liquid that has been delivered to the substrate to the predetermined quantity of API or predetermined volume of liquid. The processor 102 can determine an average quantity of API per microdroplet and/or an average volume of liquid per microdroplet. The processor 102 then adds the average quantity of API per microdroplet or average volume of liquid per microdroplet to the total quantity of API or volume of liquid that has been delivered to the substrate to arrive at a sum. The processor 102 can then determine a future difference between the resulting sum of the quantity of API or volume of liquid to the predetermined quantity of API or predetermined volume of liquid. If 1) the resulting sum of the average quantity of API per microdroplet or average volume of liquid per microdroplet and the total quantity of API or volume of liquid that has been delivered to the substrate, respectively, is greater than the predetermined quantity of API per microdroplet or predetermined volume of liquid, and 2) the future difference is less than the current difference, the processor 102 can allow for the delivery of the immediately subsequent microdroplet prior to discontinuing the delivery of microdroplets to the substrate. In one example, the processor 102 can allow for the delivery of only a single immediately subsequent microdroplet prior to discontinuing the delivery of microdroplets to the substrate. It should be appreciated in other examples that the processor 102 can discontinue the delivery of microdroplets to the substrate when the current quantity of API or total volume of liquid delivered to the substrate is greater than the desired quantity of API or predetermined total volume of liquid to be delivered to the substrate by a desired value.

Thus, the processor 102 can determine in real-time when the delivery of a select microdroplet to the substrate would cause either 1) the total volume of liquid applied to the substrate to be greater than the predetermined volume of liquid, and/or 2) the total quantity of API applied to the substrate to be greater than the predetermined quantity of API. The select microdroplet can be referred to as the immediately subsequent microdroplet. Based on this determination, and because the microdroplets have substantially the same size, the processor 102 can discontinue the delivery of microdroplets to the substrate. In particular, the processor 102 can discontinue the delivery of microdroplets to the substrate when it has been determined that the delivery of the select microdroplet would cause the total volume of liquid that has been delivered to be greater than a sum of the predetermined volume of liquid and one-half of a projected volume of the select microdroplet. It should thus be appreciated that the processor 102 can allow the select microdroplet to be delivered when the delivery of the select microdroplet causes the total volume of liquid that has been delivered to be less than the sum of the predetermined volume of liquid and one-half of a projected volume of the select microdroplet. The projected volume of the select microdroplet can be equal to a calculated average volume of liquid per microdroplet that has been delivered to the substrate, or can be projected based on any suitable alternative data.

Alternatively or additionally, the processor 102 can discontinue the delivery of microdroplets to the substrate when it has been determined that the delivery of the select microdroplet would cause the total quantity of API that has been delivered to be greater than a sum of the predetermined quantity of API and one-half of the projected quantity of API in the select microdroplet. It should thus be appreciated that the processor 102 can allow the select microdroplet to be delivered when the delivery of the select microdroplet causes the total quantity of API that has been delivered to be less than the sum of the predetermined volume of liquid and one-half of a projected quantity of API of the select microdroplet. The projected quantity of API in the select microdroplet can be equal to a calculated average quantity of API per microdroplet that has been delivered to the substrate, or can be projected based on any suitable alternative data.

Because the total quantity of API applied to the substrate can be within one-half of the quantity of API in a microdroplet with respect to the predetermined quantity of API, and because between 10 and 500 microdroplets can be delivered to a given substrate, such as between 100 microdroplets and 500 microdroplets, the total quantity of API applied to the substrate can be in a range that deviates from the predetermined desired or optimal quantity of API by an amount that is within a range from approximately 0.5% to approximately 0.1% of the predetermined quantity of API.

Similarly, because the total volume of liquid applied to the substrate can be within one-half of volume of liquid in a microdroplet with respect to the predetermined volume of liquid, and because between 100 and 500 microdroplets can be delivered to a given substrate, the total volume of liquid applied to the substrate can be in a range that deviates from the predetermined volume of liquid by an amount that is within a range from approximately 0.1% to approximately 10%, such as from approximately 0.1% to approximately 5% and for example from approximately 0.1% to approximately 0.5%, of the predetermined volume of liquid. It is recognized, of course, that as few as two microdroplets up to 500 or more microdroplets can be delivered to a given substrate as desired.

Once the processor 102 discontinues the delivery of microdroplets to the substrate, a subsequent substrate can be dosed with microdroplets in accordance with any example described above. It is thus appreciated that by controlling the dosage of API applied to each substrate in the manner described above, the control system 100 can ensure that the dosage of API delivered to each substrate is substantially equal to the predetermined or desired dosage of API. Further, the control system 100 can ensure that each substrate among a group of substrates earmarked for the same predetermined dosage can all have dosage levels that are substantially equal to each other.

When the dosing system 20 includes a plurality of dosing heads and a respective plurality of flow paths to a common substrate, the control system 100 can include respective plurality of first cameras that are each configured to image the microdroplets of a respective one of the flow paths. Thus, microdroplets that are successively delivered to the substrate along a respective flow path can each be imaged by a single first camera as they travel along the same flow path. Microdroplets successfully delivered from respective dosing heads to the substrate along respective flow paths can be imaged be a respective first plurality of first cameras. In some examples, the imaged microdroplets described above can be referred to as a first plurality of the microdroplets that are dispensed from at least one first dosing head along at least one first flow path to the substrate. As will now be described, the control system 100 can cause at least one second microdroplet to be delivered from a second dosing head to the substrate. The at least one second microdroplet can be delivered to the substrate along a corresponding second at least one flow path. The at least one second microdroplet can be configured as a plurality of second microdroplets that are successively delivered to the common substrate along a second flow path. A respective first camera 111 can image the at least one second microdroplet along the second flow path in the manner described above. In some examples, the plurality of second microdroplets can be delivered to the common substrate along a respective plurality of flow paths that are each imaged by a respective first camera 111.

The at least one second microdroplet can have a quantity of API that is less than the quantity of API in the first microdroplet. For instance, the at least one second microdroplet can be sized less than the microdroplets of the first plurality of microdroplets. Thus, the same API-containing liquid can be supplied to each of the first and second dosing heads. In another example, the at least one second microdroplet can be sized substantially equal to or even greater than the first plurality of microdroplets, but can have a second concentration of API that is less than the first concentration of API in the first plurality of microdroplets. Thus, a first reservoir of liquid containing the first concentration of API can supply the first liquid to the first dosing head, and a second reservoir containing the second concentration of API can supply the second liquid to the second dosing head.

Because a second quantity of API in the at least one second microdroplet is less than a first quantity of API in the first plurality of microdroplets, the at least one second microdroplet can be delivered when it is determined that the total quantity of API or the total volume of liquid delivered to the substrate is approaching the predetermined quantity of API or the predetermined volume of liquid, respectfully. In one example, the processor 102 can determine when the delivery of a select second microdroplet of the at least one second microdroplet to the substrate would cause the total quantity of API delivered to the substrate to be greater than the predetermined quantity of API, and in response can discontinue delivering microdroplets to the substrate. The select second microdroplet can be referred to as an immediately subsequent second microdroplet.

In another example, the processor 102 can calculate a first API difference between the predetermined quantity of API to be delivered to the substrate and the total quantity of API that would be delivered to the substrate if the immediately subsequent first microdroplet is delivered to the substrate. The processor 102 can calculate a second API difference between the predetermined quantity of API to be delivered to the substrate and the total quantity of API that would be delivered to the substrate if the at least one second microdroplet is delivered to the substrate. If the first API difference is less than the second API difference, then the processor 102 causes the immediately subsequent first microdroplet to be delivered and prevents or discontinues the delivery of the at least one second microdroplet. If the second API difference is less than the first API difference, then the processor 102 discontinues the delivery of the first microdroplets, and delivers the at least one second microdroplet to the substrate. It should be appreciated that the API differences described above can be configured as absolute values.

In one example, the processor 102 can continue the delivery of the at least one second microdroplet, which can include a plurality of second microdroplets, until the processor 102 determines that an immediately subsequent second microdroplet will cause the total quantity of API delivered to the substrate to exceed the predetermined quantity of API to be delivered to the substrate. Alternatively, the processor 102 can continue the delivery of the at least one second microdroplet, which can be configured as a plurality of second microdroplets, until the processor 102 determines that the delivery of the immediately subsequent second microdroplet to the substrate will cause the total quantity of API delivered to the substrate to be further from the predetermined quantity of API as compared to discontinuing the delivery of second microdroplets to the substrate prior to the delivery of the immediately subsequent second microdroplet. At this point, the processor 102 can discontinue the delivery of microdroplets to the substrate. When the processor 102 discontinues the delivery of microdroplets to the substrate, the processor 102 can then cause the microdroplets to be delivered to a subsequent substrate in any manner described herein.

Because the microdroplets have substantially the same size, the processor 102 can discontinue the delivery of microdroplets to the substrate when it has been determined that the delivery of the select second microdroplet would cause the total quantity of API that has been delivered to the substrate to be greater than a sum of the predetermined quantity of API and one-half of a projected quantity of API.

It should thus be appreciated that the processor 102 can allow the select second microdroplet to be delivered when the delivery of the select second microdroplet causes the total quantity of API that has been delivered to the substrate to be less than the sum of the predetermined quantity of API and one-half of a projected quantity of API. It should further be appreciated that the processor 102 can also discontinue the delivery of microdroplets to the substrate immediately after delivering the immediately subsequent second microdroplet when the quantity of API that has been delivered is greater than the predetermined quantity of API. The projected quantity of API of the select second microdroplet can be equal to a calculated average quantity of API per second microdroplet that has been delivered to the substrate, or can be projected based on any suitable alternative data.

Similarly, the processor 102 can determine when the delivery of the select second microdroplet of the at least one second microdroplet to the substrate would cause the total volume of liquid delivered to the substrate to be greater than the predetermined volume of liquid, and in response can discontinue delivering microdroplets to the substrate. In another example, the processor 102 can calculate a first volumetric difference between the predetermined volume of liquid to be delivered to the substrate and the total quantity of liquid that would be delivered to the substrate if the immediately subsequent first microdroplet is delivered to the substrate. The processor 102 can calculate a second volumetric difference between the predetermined volume of liquid to be delivered to the substrate and the total volume of liquid that would be delivered to the substrate if the at least one second microdroplet is delivered to the substrate. If the first volumetric difference is less than the second volumetric difference, then the processor 102 causes the immediately subsequent first microdroplet to be delivered and prevents or discontinues the delivery of the at least one second microdroplet. If the second volumetric difference is less than the first volumetric difference, then the processor 102 discontinues the delivery of the first microdroplets, and delivers the at least one second microdroplet to the substrate. It should be appreciated that the volumetric differences described above can be configured as absolute values.

In one example, the processor 102 can continue the delivery of the at least one second microdroplet, which can include a plurality of second microdroplets, until the processor 102 determines that an immediately subsequent second microdroplet will cause the total volume of liquid delivered to the substrate to exceed the predetermined volume of liquid to be delivered to the substrate. Alternatively, the processor 102 can continue the delivery of the at least one second microdroplet, which can be configured as a plurality of second microdroplets, until the processor 102 determines that the delivery of the immediately subsequent second microdroplet to the substrate will cause the total volume of liquid to delivered to the substrate to be further from the predetermined volume of liquid as compared to discontinuing the delivery of second microdroplets to the substrate prior to the delivery of the immediately subsequent second microdroplet. At this point, the processor 102 can discontinue the delivery of microdroplets to the substrate, and can instead cause the microdroplets to be delivered to a subsequent substrate in any manner described herein.

Because the microdroplets have substantially the same size, the processor 102 can discontinue the delivery of microdroplets to the substrate when it has been determined that the delivery of the select second microdroplet would cause the total volume of liquid that has been delivered to the substrate to be greater than a sum of the predetermined volume of liquid and one-half of a projected volume of liquid. It should thus be appreciated that the processor 102 can allow the select second microdroplet to be delivered when the delivery of the select second microdroplet causes the total volume of liquid that has been delivered to the substrate to be less than the sum of the predetermined volume of liquid and one-half of a projected volume of liquid. It should further be appreciated that the processor 102 can also discontinue the delivery of microdroplets to the substrate immediately after delivering the immediately sub-sequent second microdroplet when the volume of liquid that has been delivered is greater than the predetermined volume of liquid. The projected volume of liquid of the select second microdroplet can be equal to a calculated average volume of liquid per second microdroplet that has been delivered to the substrate, or can be projected based on any suitable alter-native data.

It should be appreciated from the description above that in some examples, the at least one second microdroplet is delivered only after the step of delivering the first plurality of microdroplets has been completed. In other examples, the at least one second microdroplet, such as a plurality of second microdroplets, can be delivered while delivering the first plurality of microdroplets. That is, at least one of the first microdroplets can be delivered to the substrate both before and after at least one second microdroplet is delivered to the substrate.

In still another example, the dosing system can include an array of dosing heads that are each configured to deliver microdroplets of a respective size that is different than the size of one or more others of the dosing heads of the array. The processor 102 can control the delivery of microdroplets from select ones of the array of dosing heads in order to dose the underlying substrate with substantially the predeter-mined volume liquid or substantially the predetermined dosage of API. The microdroplets delivered from the dosing heads of the array can have substantially the same concen-tration of API, and substantially the same API. In one example, the processor can activate a first select dosing head that delivers the largest microdroplets without exceeding the predetermined volume of liquid (or dosage of API) to deliver one or more microdroplets. Once it is determined that an immediately subsequent microdroplet from the first select dosing head will cause the total volume of liquid (or total dosage of API) delivered to the substrate to exceed the respective predetermined value, the processor can deactivate the first select dosing head activate a second select dosing head that delivers the largest microdroplets without exceed-ing the predetermined volume of liquid (or dosage of API) to deliver one or more microdroplets. It is appreciated that the microdroplets delivered by the second select dosing head are sized less than the microdroplets delivered by the first select dosing head. Once it is determined that an immedi-ately subsequent microdroplet from the first select dosing head will cause the total volume of liquid (or total dosage of API) delivered to the substrate to exceed the respective predetermined value, the processor can deactivate the sec-ond select dosing head and activate a third select dosing head that delivers the largest microdroplets without exceed-ing the predetermined volume of liquid (or dosage of API) to deliver one or more microdroplets. It is appreciated that the microdroplets delivered by the third select dosing head are sized less than the microdroplets delivered by the second select dosing head. The processor can continue selectively activating subsequent dosing heads as the actual volume of liquid (and dosage of API) approaches the respective pre-determined value, with each dosing head delivering microdroplets with a less volume than the microdroplets delivered by the preceding dosage head. The process can continue until either the predetermined volume or API has been delivered, or until the dosing head that delivers the smallest microdroplets has been activated until the immediately subsequent microdroplet would cause the total volume of liquid or dosage of API to either 1) exceed the predetermined respective value, or 2) cause a greater difference from the predetermined value as compared to not delivering the immediately subsequent microdroplet, at which point the dosing head that delivers the smallest microdroplets can be deactivated. In one example, the microdroplets delivered from the dosing head that delivers the smallest microdrop-lets can have a volume of approximately one nanoliter.

In yet another example, it is recognized that one or more variable-sized dosing heads can be configured to deliver microdroplets having differing sizes. Thus, a variable-sized dosing head can deliver one or more of its largest micro-droplet until the delivery of an immediately subsequent largest microdroplet will exceed the predetermined volume or API dosage level. At that point, the variable-sized dosing head can deliver one or more next largest microdroplets that will not cause the total volume or dosage of API to exceed the respective predetermined level, until it is determined that an immediately subsequent largest microdroplet will exceed the predetermined volume or API dosage level. The vari-able-sized dosing head can continue to selectively deliver progressively smaller microdroplets until either the total volume of liquid or dosage of API either 1) equals the respective predetermined value, or until an immediately subsequent microdroplet will 2) exceed the predetermined respective value, or 2) causes a greater difference from the predetermined value as compared to not delivering the immediately subsequent microdroplet, at which point the dosing head can be deactivated. In one example, the smallest microdroplets delivered from the dosing head can have a volume of approximately one nanoliter.

With continuing reference to FIG. 7, it should be appre-ciated that the first light source 106 and the first camera 111 can define any suitable configuration as possible. In one example, the first light source 106 and the first camera 111 can be supported by the dosing machine 74 on opposite sides of an axis that contains the flow path 110 at a location aligned with the flow path 110. Thus, the first light source 106 and the first camera 111 can be in direct alignment with each other along a direction that is oriented perpendicular to the flow path. The first beam of light 112 can travel from the first light source 106, through a microdroplet 62 to the first camera 111. If desired, one or more mirrors can direct the first beam of light 112 from the first light source, through the microdroplet 62, to the first camera 111. The first beam of light 112 can travel along a direction perpendicular to the flow path 110 as it travels through the flow path 110. Alternatively, the first beam of light 112 can travel along a direction that is oblique to the flow path 110 as it travels through the flow path.

Referring now to FIGS. 6 and 8A-8B, the at least one camera 104 can include a second detector or camera 118 that is configured to detect an optical property of each micro-droplet as it travels along the flow path from the dosing head to the substrate. Based on the optical property, the processor 102 can determine either or both of a volume of API in the microdroplet, and constituent components of the API in the microdroplet. In one example, the optical property can be a fluorescence of the API. In particular, the control system 100 can include a second light source 120 that directs a second beam of light 122 to a respective second location 124 of the flow path 110. The second location 124 of the flow path 110 can coincide with the first location or can be spaced from the first location. The second location 124 can be selected such that the microdroplets are substantially spherical at the second location 124 as described above.

The second beam of light 122 can illuminate each microdroplet in the flow path as it passes through the second location 124. In one example, the second light source 120 can be an ultraviolet (UV) light at a wavelength that provides excitation of the API in the microdroplet when the microdroplet passes through the second beam of light 122, which thereby causes the API to fluoresce without causing the solvent, which can be an alcohol or the like as described herein, to fluoresce. The fluorescence of the API causes the API to emit light at an excitation wavelength that is different than wavelength of the UV light of the second light source 120. The excitation wavelength is received by the second camera 118 that converts the light to a voltage that can be detected by any suitable apparatus such as an electrical circuit, and in some examples a voltmeter. Based on a prior calibration that correlates voltage to the concentration of the fluorescing API in the microdroplet, the processor can determine the actual concentration of API in each microdroplet that passes through the second beam of light 122 along the respective flow path.

As shown in FIGS. 8A-8B, the second beam of light 122 can reflect off of at least one mirror 126 as it travels from the second light source 120 to the second camera 118. The second light source 120 and the second camera 118 can be structurally configured and positioned such that a plane that passes through each of the second light source 120 and the second camera 118 also intersects the flow path. Otherwise stated, an entirety of the second beam of light 122 can lie in the plane that intersects the flow path. Further, the second light source 120 and the second camera 118 can be in front of the flow path, while the mirror 126 can be disposed behind the flow path. The second beam of light 122 can intersect the flow path as it travels from the mirror 126 to the second camera 118. Alternatively, the second beam of light 122 can intersect the flow path as it travels from the second light source 120 to the mirror 126 as desired.

Referring now to FIG. 8C, the at least one camera 104 can include a third detector or camera 128 that is configured to detect a Raman and/or Resonance Raman scattering spectrum of the API of each microdroplet as it travels along the flow path 110 from the dosing head 46 to the substrate. Based on the detected peak wavelengths in the Raman and/or Resonance Raman scattering spectrum, the processor 102 can determine the molecular identity of each of the constituent components of the API in the microdroplet, which can be any combination of the multitude of cannabis molecules. In particular, the control system 100 can include a third light source 130 that directs a third beam of light 132 to a respective third location 134 of the flow path 110. The third location 134 of the flow path 110 can coincide with either or both of the first and second locations or can be spaced from each of the first and second locations. The third location 134 can be selected such that the microdroplets are substantially spherical at the second location 124 as described above.

The third beam of light 132 can illuminate each microdroplet in the flow path as it passes through the second location 124. In one example, the third light source 130 can be a laser light at a wavelength that produces the Raman and/or Resonance Raman scattering when it travels through the API of each microdroplet. Based on the Raman and/or Resonance Raman scattering, the processor 102 can deter-mine the molecules of the API in each microdroplet, thereby ensuring that the API in each microdroplet has the predetermined desired constituent components. Further, based on the Raman and/or Resonance Raman scattering, the processor 102 can determine that the API is consistent among the microdroplets being delivered to a common substrate. In another example, the third light source 130 or an additional light source can be configured as an X-Ray that produces X-Ray scattering to identify the constituent components of the API.

The third beam of light 132 can reflect off of at least one mirror 126 (see FIG. 8B) as it travels from the second light source 120 to the second camera 118 in the manner described above with respect to the second beam of light 122 shown in FIG. 8B. The third light source 130 and the third camera 128 can be spaced from the second light source 120 and the second camera 118 along the axis that defines the flow path. The third beam of light 132 can reflect from the same mirror as the second beam of light 122 or a different mirror. Alternatively, the third light source 130 and the third camera 128 can be coplanar with the second light source 120 and the second camera 118, but the angle of incidence and reflection from the mirror 126 can be different than that of the second beam of light 122. The third beam of light 132 can intersect the flow path as it travels from the mirror 126 to the third camera 128. Alternatively, the third beam of light 132 can intersect the flow path as it travels from the third light source 130 to the mirror as desired. Alternatively still, the third beam of light 132 can travel from the third light source 130 through the flow path to the third camera 128 without passing through any reflective surfaces.

It should be appreciated that any two or more up to all of the cameras described above, or additional cameras as desired, can be operated simultaneously so as to image the same microdroplets as they are dispensed from the dosing head 46. It should be further appreciated that any one of the cameras described above, or an additional camera, can be operated simultaneously to detect the presence of each microdroplet that travels along the respective flow path. The processor can count the number of microdroplets delivered to each substrate. In still other examples, the control system 100 can perform reflectometry of the microdroplets and/or interferometry of the microdroplets, both of which can reveal optical signatures of the API and/or the solvent of the microdroplet. It should therefore be appreciated that any one of the cameras described above, or an additional camera as desired, can noninvasively detect any optical property as desired of the microdroplet or API thereof. For instance, the optical property can be a vibration. In another example, the optical property can be a fluorescence. In another example, the optical property can be a Raman and/or Resonance Raman scattering. In another example, the optical property can be an X-ray scattering. In another example, the optical property can be an absorption of infrared photons that can reveal an optical signature of the API and/or solvent of the microdroplet. In this regard, the at least one light source can be configured as an infrared light source that can direct a beam of infrared light through the microdroplet in accordance with any example described above or any suitable alternative example. Any of the above optical diagnostic systems can be expanded to a holographic format to produce a three-dimensional representation of one or more desired optical properties. The processor 102 can generate a hologram of the imaged microdroplet that can include the dimensions and optical properties of the microdroplet that were obtained using any of the above-described methods. In other examples, the processor 102 can generate the dimensions and optical properties of the microdroplet that were obtained using any of the above-described methods in tabular form.

Methods and Systems for Adding Cannabis to Edible Products

It should be appreciated from the description above that methods and apparatus are provided for transforming an edible products or other substrates into an accurately and repeatably and precisely dosed cannabis or other API-containing products. As will be described, the edible products or other substrates can be consistently dosed to avoid substantial variations in API dosage levels among a group of edible products or other substrates that are intended to have the same dosage of API. The method can include the step of delivering the cannabis to the substrate, which can be an edible product or non-edible product. The delivering step can be performed with any suitable one or more applicators that deliver a predetermined dose of the cannabis. The term "cannabis" as used herein refers to any extract from a marijuana plant or hemp plant, such as CBD, THC, or any alternative cannabinoid, alone or in combination with any one or more of a flavonoid or terpene. The extract can be in its pure form or processed as desired, including as example, emulsified forms of cannabis fluids. While this disclosure provides for the addition of at least one cannabis to a substrate, and thus cannabis is contemplated as a market for the final product, applications of the systems and methods disclosed herein are possible and envisioned that do not involve cannabis, including (but not limited to) other active pharmaceutical ingredients (API). For instance, applications of the systems and methods disclosed herein are possible and envisioned to include active pharmaceutical ingredients (APIs) including one or more cannabinoids, any alternative one or more over-the-counter (OTC) or prescription drugs including those that provide one or both of a health benefit or recreational drug experience, or otherwise controlled ingestible materials. Thus, reference herein to an active pharmaceutical ingredient can include any one or more up to all of the following: cannabis and cannabis plant-derived compounds, including one or more cannabinoids in either natural oily forms or emulsified forms, one or more over-the-counter drugs, one or more prescription drugs, one or more flavonoids, and one or more terpenes. Reference herein to an active pharmaceutical ingredient can alternatively or/additionally include one or more up to all of the following: psychedelic or hallucinogenic ingredients such as psilocybin and psilocyn, and synthetic opioids including synthetic opioid pain reducers. While accurately dosed synthetic opioids can replace the more dangerous ingredients such as fentanyl, it should be appreciated that the API can alternatively or additionally include fentanyl, recognizing the accurate dosage of the type described herein can be of importance when administering an API that can have severe consequences when inaccurate dosages are administered. Similarly, reference to one or more of the active pharmaceutical ingredients identified above can apply equally to any other of the active pharmaceutical ingredients identified above. According to an aspect of the present disclosure, a method of delivering a cannabis or conventional drug may also be used to deliver homeopathic remedies, herbal supplements with flavors or odors, and so forth to an edible product. The resulting edible product can be referred to as a "nutraceutical," as its definition is "a food containing health-giving additives or having medicinal benefit."

The active pharmaceutical ingredient can be added to a substrate to produce an active-containing substrate, which can include edible food products, edible non-food products, or other inedible substrates. Edible food products can include, by way of example and not limitation, hard candy, chocolates brownies, cookies, soft candies such as gummy candy, savories such as trail mix bars or dried meat pieces, and the like. Thus, in some examples, the edible food products can be cooked food product. In some specific examples, the edible food products can be baked food product. Edible food product can be bite sized, such as M&M candy, gummy candies, chocolate kisses, or the like, or can be designed to require more than one bite for full consumption, such as a cookie. Thus, in some examples, the edible food product can include a plurality of mixed ingredients. As will be appreciated from the description below, the food product can be fully prepared prior to addition of the API to the food product. In other examples, the API can be added during preparation of the food product. In some examples, the food products can be a dehydrated food product, such as dried fruit or jerky. In other examples, the edible product can be freeze dried. In still other examples, the edible product can be a raw food product, such as nuts or fruit.

It will be appreciated that the application of the active pharmaceutical ingredient to the food product can allow for a broader range of food product to be made with active pharmaceutical ingredients. Further, the API can be more accurately dosed compared to conventional methods. When the active pharmaceutical ingredients are applied to previously prepared food product, APIs having short shelf lives can be applied to the substrate and ingested in a shorter period of time with respect to active pharmaceutical ingredients that are combined with the raw ingredients that are then processed to prepare the food product. When the API is added during the food preparation process, the API can be more accurately dosed compared to conventional methods whose API is included in bulk ingredients that are mixed prior to cooking or baking.

In still other examples, .as described above, the substrate that is dosed with the API can be an edible non-food product. While the primary purposes of a food product is the delivery of nutrients, the primary purposes of non-food products is to deliver an API, either alone or with a carrier. Examples of edible non-food products can include a dissolvable material, such as a slip, or can be a capsule, pill, tablet, nugget, or the like. Alternatively still, as noted above, the substrate can be an inedible product 33. That is, the substrate is not designed for human consumption, but is designed to be placed into the mouth. One such nonlimiting example is a tongue depressor 35 (see FIG. 5E).

In one aspect, a plurality of active-containing substrates can be provided as a set, wherein some of the substrates have different dosages of the active pharmaceutical ingredients and are designed to be ingested at different times among a period of time, such as different days of the week. Thus, a desired dosage profile can be delivered to the patient throughout the period of time. Alternatively or additionally, one of the active-containing substrates can contain a different at least one active pharmaceutical ingredient. Thus, the set of active-containing substrates can be designed to be sequentially ingested (that is, ingested one after the other) over the period of time, thereby delivering a desired predetermined sequence of active pharmaceutical ingredients to the patient.

The API-containing liquid can be in the form of a pure API, such as a resin, or can be in the form of a concentration of API in a liquid carrier such as a solvent. The API-containing solid can be in the form of pure API, such as a powder, or can be a mixture of the API with any other suitable material. API-containing liquids and API-containing powders to be delivered to a substrate can be referred to as API-containing material. In some examples, an applicator can deliver microquantity of the active pharmaceutical ingredient to the substrate. For instance, the microquantity can be carried by a solvent and delivered by the applicator as microdroplets each having a volume in a range from approximately 2 nanoliters to approximately 10 microliters, such as from approximately 25 nanoliters to approximately 2 microliters. For instance, the microdroplets can have a volume that is in a range from approximately 25 nanoliters to approximately 1 microliter. The microdroplets can have a concentration of API as desired. For instance, the concentration of API can range from approximately 50 micrograms per microliter of solution to approximately 1 milligram per microliter of solution. In other examples, the liquid can be a pure resin of the API.

It is envisioned in one example that applicators delivering like dosages of API to like substrates can deliver approximately the same sized microdroplets to the like substrates. Thus, for instance when delivering the API to dried fruits and/or nuts designed to have the same dosage of API, the applicators can deliver the approximately same volume and number of microdroplets to each dried fruit and/or nut, or to a group, such as a serving, of dried fruits and/or nuts.

As will be described in more detail below, dosing heads can be provided that are configured to deliver microdroplets of any suitable volume, such as the volumes described above. Therefore, each microdroplet can contain a microquantity of API in a range from approximately 0.1 micrograms to approximately 10 milligrams, such as from approximately 1 milligram to approximately 2 milligrams. It is recognized, however, that the microdroplets can have any volume as desired. Further, it is recognized that each microdroplet can contain different quantities of API depending, for instance, on the volume of the microdroplet. The microquantity of API in a microdroplet can allow the dosage of API delivered to a substrate to be accurately and precisely controlled. For instance, the respective volumes of microdroplets can be delivered to a substrate within a range from approximately 1% to approximately 10%, for instance approximately 5%, from a target volume of microdroplets at three sigma. Thus, the dosage of API in each microdroplet can be delivered to the substrate within a range from approximately 1% to approximately 10%, for instance approximately 5%, from a target dosage at three sigma. The target volume of microdroplets can vary based on the surface area or volume of the substrate to which the microdroplets are to be applied. Similarly, the dosage of API to be delivered to a substrate can likewise be within a range from approximately 1% to approximately 10%, for instance approximately 5% at three sigma, from a target dosage of API to the substrate or a serving of packaged substrates, such as dried fruits or nuts. The target volume of microdroplets can vary based on the surface area or volume of the substrate to which the microdroplets are to be applied.

Thus, in one example, the microquantity can be delivered to a substrate in the form of microdroplets. The use of microdroplets may help in accurate and precise dosage administration of the active pharmaceutical ingredient compared to conventional techniques. The microdroplets can be delivered to an outer surface of the substrate by a 3D printer, inkjet printer, or other suitable printing process. Alternatively or additionally, the microdroplets can be delivered to the outer surface of the substrate by precision spraying. Alternatively or additionally still, the microdroplets can be delivered to an internal location of the substrate that is surrounded by the outer surface. For instance, the microdroplets can be delivered with an air gun that shoots the microdroplets toward the substrate in a burst of high-pressure air (in an analogous way to how some vaccines and other drugs may be administered subcutaneously without injections with needles). Without being bound by theory, it is believed that the microdroplets to an internal location of the substrate may also assist in facilitating administration or ingestion of potentially bitter-tasting (or strongly cannabis-tasting) formulations by providing a means to add small amounts of such material to a much larger amount of edible product.

The microdroplets including the API can be delivered to the substrate. The microdroplets can include a solution that includes the at least one cannabis in its liquid form as the solute mixed with any suitable solvent. In order to assist in achieving predictable doses of the at least one cannabis, the at least one cannabis can be substantially homogeneously mixed with the solute. Alternatively, the microdroplets can consist of or consist essentially of the cannabis extract, either purified, partially purified, or unpurified, in liquid form having a desired viscosity that allows for the cannabis extract to be reliably dispensed. In some examples, the liquid can be heated to achieve the desired viscosity without mixing the cannabis extract in a solute. In some examples, the microdroplets can have an oily or hydrophilic nature. For instance, microdroplets may be multilayered, with a protein or other protective coating surrounding a precise dosage of an oil-based or water-based formulation. Because the concentration of the cannabis in the liquid can be known, a volume of liquid can be predetermined and delivered to the substrate to achieve a desired predetermined approximate dose of the cannabis. In some other examples, the microdroplets may be of an emulsified cannabis liquid.

In other aspects, the active pharmaceutical ingredient, which can include one or more cannabinoids, terpenes, and/or flavonoids, can be added to the substrate in a granular form. For instance, the cannabis extract, which can be purified, partially purified, or unpurified, can be delivered to the substrate as a powder. In some examples, the cannabis can be crystallized and ground to produce the powder. Because the concentration of the cannabis in the powder can be known, a mass of the powder can be predetermined and delivered to the substrate to achieve a desired dose of the cannabis.

The liquid or powder to be delivered to the substrate can include a single desired cannabis. Thus, the single desired cannabis can be delivered to the substrate. Alternatively, a plurality of different liquids or powders can be delivered to the substrate, each containing their own different one or more cannabis ingredients. Accordingly, by delivering multiple different liquids and powders, a plurality of desired cannabis ingredients can be delivered to the substrate. The liquids and powders can be delivered in the same quantity or in different quantities. Accordingly, the ratio of one or more cannabis ingredients relative to one or more other cannabis ingredients can be controlled. In other examples, the liquid or powder to be delivered to the substrate can include a plurality of cannabis ingredients, either in equal proportions or in desired ratios. Thus, a single liquid or powder can be delivered to the substrate to deliver either a single cannabinoid or a plurality of cannabis ingredients. The plurality of cannabis ingredients delivered to the food product with one or more powders or liquids can include greater than one cannabis ingredient up to the full range of cannabis ingredients, such as approximately 113 cannabinoids.

In some aspects, formulations used for addition to edible products may comprise a substantial fraction of a plurality of any suitable cannabinoids. Non-limiting examples of such cannabinoids include THC or CBD, or of a combination of one or both of these and other cannabinoids. In some aspects, the API can include terpenes or flavonoids alone or in combination with one or more cannabinoids. The terpenes and/or flavonoids can be extracted from cannabis or hemp, or could be provided as pure substances acquired or synthesized commercially from other sources. Further, bitter or strong cannabis flavors may be hidden within the much more prevalent flavor of the "host" edible product. Alternatively or additionally, the at least one cannabinoid can be deposited on a location of a product that is not designed to be brought into direct initial contact with the tongue during ingestion, thereby further masking the taste of the at least one cannabinoid. For instance, the at least one cannabinoid can be applied to the top rounded surface of a cookie, it being recognized that cookies are designed to be placed into the mouth with the bottom flat surface against the tongue. Alternatively or additionally, the microdroplets can be coated with a sugar or other suitable taste-masking agent as desired.

In some aspects, soft edible products such as chocolate, gummies, licorice, and the like can be used as a "carrier" or "host" for a quantity of cannabinoid that can be injected into the soft edible product (by air gun, or by needle, or by other suitable methods known in the art), to push the added material into the bulk of the soft edible product. Cannabis flavors may be masked by such an approach. In some aspects, energy such as infrared light, forced air, or microwaves may be applied to a surface of an edible product to soften (or further soften) the material in a small area, and cannabis or hemp-derived material may be injected into the area pre-treated with infrared more easily (or to a great depth in the host edible product). The energy can be applied before injection, after injection, or both before and after injection. In other examples, the at least one cannabis can be applied to multiple surfaces of the edible product up to all surfaces of the edible product.

In some aspects, the at least one cannabis can be mixed in with food ingredients, particularly when such ingredients are suitable for addition, shortly prior to packaging or delivering a prepared edible product (for example, as an ingredient in an icing or other coating, or as part of the sugar coating applied to gummy candies. In some aspects, an edible product can be coated with small oil spheres or a coating of solid powder, each containing the at least one cannabis, to block taste or hide cannabinoid flavor. In some aspects, colorant may be added to the at least one cannabis prior to delivering the at least one cannabis to the edible product, in order to blend the formulation blend with the coloring of the edible product.

According to an aspect, the applicator can deliver successive microdroplets containing the API to the underlying substrate under gravitational forces. In another aspect, the applicator can deliver successive microdroplets containing the API to the underlying substrate under positive pressure, where the positive pressure and gravitational forces contribute to the velocity of the microdroplet as it travels from the applicator to the substrate. In some aspects the microdroplets travel along a vertical path to the underlying substrate. In other examples the path can include a horizontal directional component.

According to an aspect, energy is added to a surface of the edible product to increase adhesion of the API-containing material to the edible product. According to an aspect, energy is added to increase a temperature at the surface. In one aspect, the temperature can be increased by directing at least one of forced air, microwaves, and light, such as infrared light, to the surface. The energy can be added prior to delivering the API-containing material to the edible product, after delivering the API-containing material to the edible product, or both before and after delivering the API-containing material to the edible product.

It should be noted that the illustrations and discussions of the embodiments and examples shown in the figures are for exemplary purposes only and should not be construed limiting the disclosure. One skilled in the art will appreciate that the present disclosure contemplates a range of possible modifications of the various aspects, embodiments and examples described herein. Additionally, it should be understood that the concepts described above with the above-described embodiments and examples may be employed alone or in combination with any of the other embodiments and examples described above. It should further be appreciated that the various alternatives described above with respect to one illustrated embodiment can apply to all other embodiments and examples described herein, unless otherwise indicated. Reference is therefore made to the claims.

What is claimed:

1. A method of limiting error rates in an API dosing system, the method comprising the steps of:
   delivering microdroplets of a liquid successively from at least one dosing head to a substrate along a path, wherein the liquid contains a quantity of active pharmaceutical ingredient;
   imaging the successively delivered microdroplets at a location between the at least one dosing head and the substrate along the path; and
   based on the imaging step, determining a total volume of the liquid that has been delivered to the substrate;
   comparing the total volume of liquid that has been delivered to the substrate to a predetermined volume of liquid to be delivered to the substrate; and
   discontinuing the delivering step when the total volume is within a selected tolerance, wherein the selected tolerance is within 10% of the predetermined volume of liquid.

2. The method of claim 1, wherein the selected tolerance is 1%.

3. The method of claim 1, further comprising the step of determining in real time when delivery of a select microdroplet to the substrate would cause the total volume of liquid to be greater than the predetermined volume of liquid.

4. The method of claim 3, comprising the step of discontinuing the delivering based on the determining step.

5. The method of claim 4, comprising performing the step of discontinuing prior to delivering the select microdroplet when the delivery of the select microdroplet would cause the total volume of liquid that has been delivered to be greater than a sum of the predetermined volume of liquid and one-half of a projected volume of the select microdroplet.

6. The method of claim 5, comprising the step of allowing the select microdroplet to be delivered when the delivery of the select microdroplet causes the total volume of liquid that has been delivered to be less than the sum of the predetermined volume of liquid and one-half of a projected volume of the select microdroplet.

7. The method of claim 5, comprising performing the step of discontinuing immediately after delivering the select microdroplet when the total volume of liquid that has been delivered is greater than the predetermined volume of liquid.

8. The method of claim 1, wherein all microdroplets are delivered successively from a single dosing head, and the imaging step comprises imaging each of the microdroplets with a single camera.

9. The method of claim 2, wherein the delivering step comprises a delivering a first plurality of the microdroplets from a first dosing head to the substrate, and delivering at least one second microdroplet from a second dosing head to the substrate.

10. The method of claim 9, wherein the at least one second microdroplet is sized less than the microdroplets of the first plurality of the microdroplets.

11. The method of claim 10, further comprising the step of determining in real time when delivery of a select second microdroplet of the at least one second microdroplet to the substrate would cause the total volume of liquid to be greater than the predetermined volume of liquid.

12. The method of claim 11, comprising the step of discontinuing the delivering step based on the determining step when it is determined that delivery of the select second microdroplet of the at least one second microdroplet to the substrate would cause the total volume of liquid to be greater than the predetermined volume of liquid.

13. The method of claim 12, comprising performing the discontinuing step prior to delivering the select second microdroplet when the delivery of the select second microdroplet would cause the total volume of liquid that has been delivered to be greater than a sum of the predetermined volume of liquid and one-half of a projected volume of the select second microdroplet.

14. The method of claim 13, comprising the step of allowing the select second microdroplet to be delivered when the delivery of the select second microdroplet causes the total volume of liquid that has been delivered to be less than the sum of the predetermined volume of liquid and one-half of a projected volume of the select second microdroplet.

15. The method of claim 14, comprising performing the discontinuing step immediately after delivering the select second microdroplet when the total volume of liquid that has been delivered is greater than the predetermined volume of liquid.

16. The method of claim 1, wherein the imaging step is performed at a location along the path whereby the microdroplets are substantially spherical.

17. The method of claim 1, wherein the imaging step is performed along a trajectory that intersects the path.

18. The method of claim 1, wherein the API comprises *cannabis*.

19. The method of claim 18, wherein the *cannabis* comprises a cannabinoid including at least one of TCH and CBD.

20. The method of claim 1, wherein the API comprises at least one terpene.

21. The method of claim 1, wherein the API comprises at least one of psilocybin and psilocyn.

22. The method of claim 1, wherein the API comprises a synthetic opioid.

* * * * *